US012119103B2

(12) United States Patent
Mork

(10) Patent No.: US 12,119,103 B2
(45) Date of Patent: Oct. 15, 2024

(54) GANs FOR LATENT SPACE VISUALIZATIONS

(71) Applicant: Tempus AI, Inc., Chicago, IL (US)

(72) Inventor: Ryan Mork, Chicago, IL (US)

(73) Assignee: Tempus AI, Inc., Chicago, IL (US)

(*) Notice: Subject to any disclaimer, the term of this patent is extended or adjusted under 35 U.S.C. 154(b) by 348 days.

(21) Appl. No.: 17/648,936

(22) Filed: Jan. 25, 2022

(65) Prior Publication Data
US 2022/0319675 A1 Oct. 6, 2022

Related U.S. Application Data

(60) Provisional application No. 63/200,823, filed on Mar. 30, 2021.

(51) Int. Cl.
G16H 30/40 (2018.01)
G06N 3/123 (2023.01)
G06T 7/00 (2017.01)

(52) U.S. Cl.
CPC ............. *G16H 30/40* (2018.01); *G06N 3/123* (2013.01); *G06T 7/0012* (2013.01)

(58) Field of Classification Search
CPC ........ G16H 30/40; G16H 50/20; G06N 3/123; G06N 3/045; G06N 3/0464; G06N 3/047; G06N 3/0475; G06N 3/094; G06N 20/00; G06T 7/0012; G06T 2207/10024; G06T 2207/10056; G06T 2207/20081; G06T 2207/20084; G06T 2207/30024; G06T 2207/30096; G16B 25/10; G16B 40/20
See application file for complete search history.

(56) References Cited

U.S. PATENT DOCUMENTS

| | | | |
|---|---|---|---|
| 11,514,289 B1* | 11/2022 | Otte | G06N 20/00 |
| 2013/0044927 A1* | 2/2013 | Poole | G06T 7/0014 |
| | | | 382/128 |
| 2017/0357844 A1* | 12/2017 | Comaniciu | G16H 30/00 |
| 2020/0098448 A1 | 3/2020 | Shah et al. | |
| 2020/0211716 A1 | 7/2020 | Lefkofsky et al. | |
| 2020/0335102 A1 | 10/2020 | Lefkofsky et al. | |
| 2020/0335187 A1 | 10/2020 | Lefkofsky et al. | |

(Continued)

FOREIGN PATENT DOCUMENTS

WO 2020081795 A1 4/2020

OTHER PUBLICATIONS

Inkawhich, Dcgan Tutorial, https://pytorch.org/tutorials/beginner/dcgan_faces_tutorial.html, Copyright 2017, PyTorch, 11 pages.

(Continued)

*Primary Examiner* — Md K Talukder
(74) *Attorney, Agent, or Firm* — Quarles & Brady LLP

(57) ABSTRACT

The disclosure provides a method of analyzing a patient. The method includes receiving a plurality of latent space representations of patient data including genetic data associated with a plurality of patients, providing each of the plurality of latent space representations to a trained model, receiving a plurality of images from the trained model, each image included in the plurality of images being associated with a patient included in the plurality of patients, grouping at least a portion of the plurality of images into a plurality of groups, and displaying the plurality of groups to at least one user.

20 Claims, 18 Drawing Sheets

(56) References Cited

U.S. PATENT DOCUMENTS

2020/0365232 A1   11/2020  Jaros et al.
2021/0090694 A1*  3/2021  Colley .................. G16H 15/00
2021/0233664 A1   7/2021  Colley et al.
2022/0319675 A1*  10/2022  Mork .................. G06N 3/0464

OTHER PUBLICATIONS

Radford et al., Unsupervised Representation Learning with Deep Convolutional Generative Adversarial Networks, arXiv:1511.06434, Jan. 7, 2016, pp. 1-16.
U.S. Appl. No. 63/067,748 Specification, filed Aug. 19, 2020, 79 pages.
Wikipedia, Chernoff Face, https://en.wikipedia.org/wiki/Chernoff_face, Apr. 26, 2021, 3 pages.

* cited by examiner

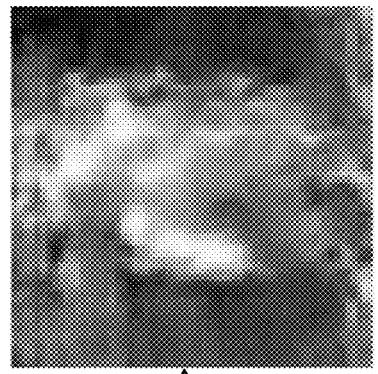
Fig. 11C
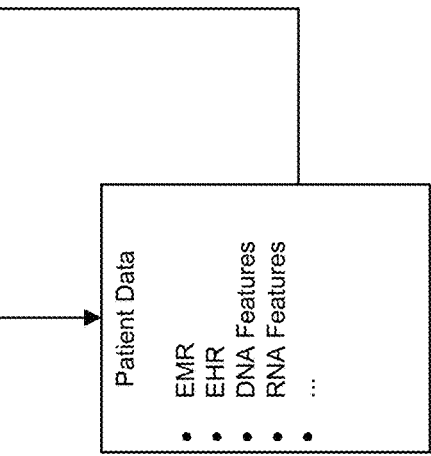
Fig. 11D
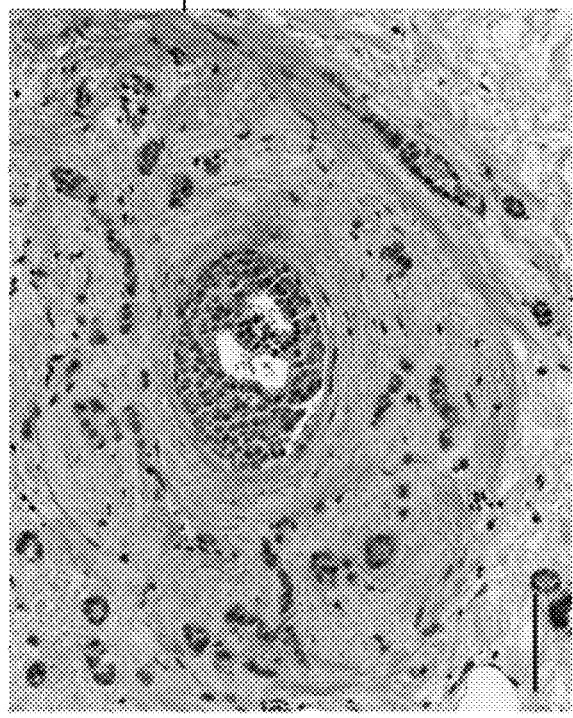
Fig. 11A
Fig. 11B

GANs FOR LATENT SPACE VISUALIZATIONS

CROSS-REFERENCE TO RELATED APPLICATIONS

This application claims the benefit of priority to U.S. provisional application 63/200,823, filed Mar. 30, 2021, the contents of which are incorporated by reference herein in their entirety.

BACKGROUND

Identifying trends within data is oftentimes difficult to perform reliably. Some trends are artifacts of the data while others may be spurious to the overall information. In some examples, identified trends may even be correlated with innocuous metrics, such as which institution recorded a testing result or performed the data intake process.

Genetic data can include large dimensions of data. For example, RNA sequencing data can include over ten thousand read values corresponding to the gene activity levels. Due to the high dimensionality of RNA data, it can be difficult to identify patterns, indicators, and other data useful for treating patients (e.g., diagnosing patients, prescribing appropriate treatments for patients, etc.).

Accordingly, there is a need in the art to identify trends and correlations within a data set which are effective and easily enable a reviewer (e.g., an oncologist) to identify and follow the meaningfulness of the depicted trend or correlation within underlying data.

SUMMARY OF DISCLOSURE

Disclosed herein are systems, methods, and mechanisms useful for automatically analyzing genetic data. In particular, the disclosure provides systems, methods, and mechanisms for analyzing patients by using latent space representations of genetic data to generate patient images, and grouping patients based on the patient images.

In accordance with some embodiments of the disclosed subject matter, a method of analyzing a patient is provided. The method includes receiving a plurality of latent space representations of patient data including genetic data associated with a plurality of patients, providing each of the plurality of latent space representations to a trained model, receiving a plurality of images from the trained model, each image included in the plurality of images being associated with a patient included in the plurality of patients, grouping at least a portion of the plurality of images into a plurality of groups, and displaying the plurality of groups to at least one user.

In accordance with some embodiments of the disclosed subject matter, a method of analyzing a patient is provided. The method includes receiving first genetic data including at least one of RNA data or DNA data associated with a patient, generating second genetic data based on the first genetic data, the second genetic data having a lower dimensionality than the first genetic data, providing the second genetic data to a trained model, receiving a patient image representative of the second genetic data from the trained model, identifying a pattern in the patient image that is present in at least one other image in a set of images generated by the trained model, providing the patient image to an analysis engine, receiving patient information from the analysis engine, and causing the patient information to be output to at least one of a medical practitioner or a memory.

In accordance with some embodiments of the disclosed subject matter, a method of generating a medical analysis of a patient is provided. The method includes receiving first genetic data including at least one of RNA data or DNA data associated with a patient, generating second genetic data based on the first genetic data, the second genetic data having a lower dimensionality than the first genetic data, providing the second genetic data to a trained model, receiving a patient image representative of the second genetic data from the trained model, identifying a pattern in the patient image that is present in at least one other image in a set of images generated by the trained model, providing the patient image to an analysis engine, receiving patient information from the analysis engine, generating a report based on the patient information, and causing at the report to be output to at least one of a medical practitioner or a memory.

In accordance with some embodiments of the disclosed subject matter, a genetic data analysis system including at least one processor and at least one memory is provided. The system is configured to receive first genetic data including at least one of RNA data or DNA data associated with a patient, generate second genetic data based on the first genetic data, the second genetic data having a lower dimensionality than the first genetic data, provide the second genetic data to a trained model, receive a patient image representative of the second genetic data from the trained model, identify a pattern in the patient image that is present in at least one other image in a set of images generated by the trained model, provide the patient image to an analysis engine, receive patient information from the analysis engine, and provide the patient information to at least one of a medical practitioner or a memory.

In accordance with some embodiments of the disclosed subject matter, a method of analyzing a patient. The method includes receiving first genetic data including at least one of RNA data or DNA data associated with a patient, generating second genetic data based on the first genetic data, the second genetic data having a lower dimensionality than the first genetic data, providing the second genetic data to a trained model, receiving a patient image representative of the second genetic data from the trained model, generating a cluster including the patient image and a subset of a set of images generated by the trained model, the set of images associated with a group of patients, providing the cluster to an analysis engine, receiving patient information from the analysis engine, and causing the patient information to be output to at least one of a medical practitioner or a memory.

BRIEF DESCRIPTION OF DRAWINGS

FIG. 11A is a sample breast cancer ductal carcinoma in situ (DCIS) H & E slide.

FIG. 11B is exemplary patient data.

FIG. 11C is an exemplary latent space representation of RNA.

FIG. 11D is an image generated using a trained model based on the latent space representation in FIG. 11C.

DETAILED DESCRIPTION

Figure 1:
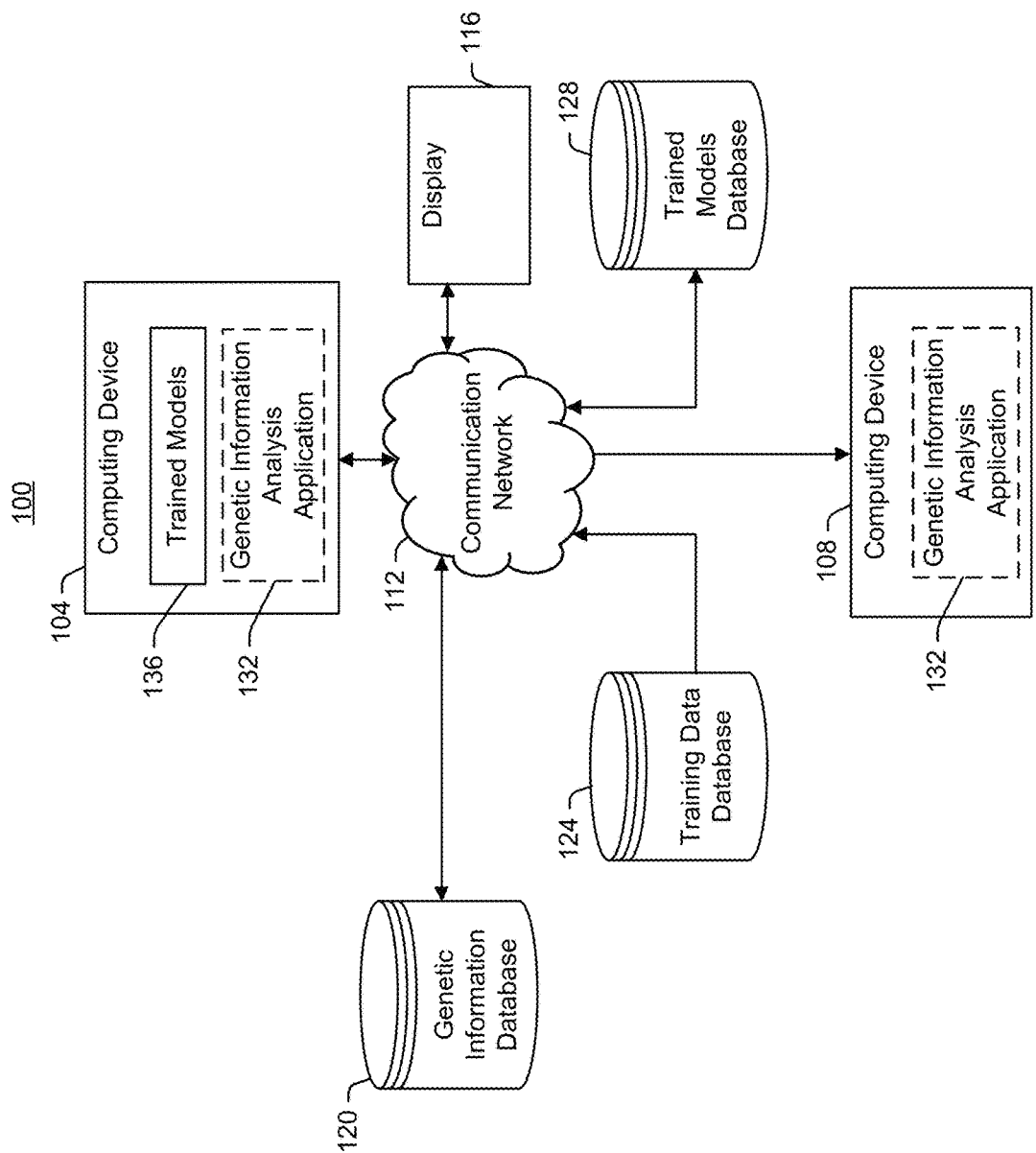
FIG. 1 is an example of a system for analyzing genetic data.

The various aspects of the subject disclosure are now described with reference to the drawings. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions, rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips, etc.), optical disks (e.g., compact disk (CD), digital versatile disk (DVD), etc.), smart cards, and flash memory devices (e.g., card, stick).

Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Computer vision modeling has been applied to some types of data to identify, for example, a measurable latent attribute which is missing from one set of data (a smile or glasses) and adding that latent attribute in based on the differences observed in another set of data with a generative adversarial network (GAN) as described in "Unsupervised Representation Learning With Deep Convolutional Generative Adversarial Networks" by Alec Radford, Luke Metz, and Soumith Chintala, which is incorporated by reference in its entirety. While image representations of latent attributes have been explored, generating new images from a latent space without first training the GAN only to predict a latent attribute which was present in a previous image set.

It would be advantageous to train a GAN which may generate new images from latent attributes which an observer may identify as distinct from the average image as generated from the GAN for the novel detection of new latent attributes in an underlying encoded data set As used herein, "cancer" shall be taken to mean any one or more of a wide range of benign or malignant tumors, including those that are capable of invasive growth and metastases through a human or animal body or a part thereof, such as, for example, via the lymphatic system and/or the blood stream. As used herein, the term "tumor" includes both benign and malignant tumors and solid growths. Typical cancers include but are not limited to carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukemia, Hodgkin's disease, small cell carcinoma of the lung, melanoma, neuroblastoma, glioma, and soft tissue sarcoma of humans.

FIG. 1 shows an example of a system 100 for analyzing genetic data. In some embodiments, the system 100 can include a computing device 104, a secondary computing device 108, and/or a display 116. In some embodiments, the system 100 can include a genetic information database 120, a training data database 124, and/or a trained models database 128. In some embodiments, the trained models database 128 can include one or more trained machine learning models such as artificial neural networks. In some embodiments, the computing device 104 can be in communication with the secondary computing device 108, the display 116, the genetic information database 120, the training data database 124, and/or the trained models database 128 over a communication network 112. As shown in FIG. 1, the computing device 104 can receive genetic information, such as RNA count data, and generate images representative of the RNA count data. As will be described further below, the genetic information can include latent space representations of raw RNA count data. In some embodiments, the computing device 104 can execute at least a portion of a genetic information analysis application 132 to automatically generate images representative of genetic data.

The genetic information analysis application 132 can be included in the secondary computing device 108 that can be included in the system 100 and/or on the computing device 104. The computing device 104 can be in communication with the secondary computing device 108. The computing device 104 and/or the secondary computing device 108 may also be in communication with a display 116 that can be included in the system 100 over the communication network 112.

The communication network 112 can facilitate communication between the computing device 104 and the secondary computing device 108. In some embodiments, communication network 112 can be any suitable communication network or combination of communication networks. For example, communication network 112 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, etc.), a wired network, etc. In some embodiments, communication network 112 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

The genetic information database 120 can include raw count data (e.g., RNA count data and/or DNA count data) and/or latent space representations of the raw count data. In some embodiments, the genetic information database 120 can include images generated by the genetic information analysis application 132 based on latent space representations of the raw count data.

The training data database 124 can include a number of images for training a model to generate images representative of the latent space representations of the raw count data.

In some embodiments, the training data image database 124 can include object images (e.g., images of an airplane, a bird, a car, a cat, a deer, a dog, a horse, a monkey, a ship, a truck, etc.). In some embodiments, the training data image database 124 can include cell images (e.g., slide images from a microscope).

The trained models database 128 can include a number of trained models that can receive latent space representations of the raw count data and output images representative of the latent space representations. In some embodiments, trained models 136 can be stored in the computing device 104.

Figure 2:
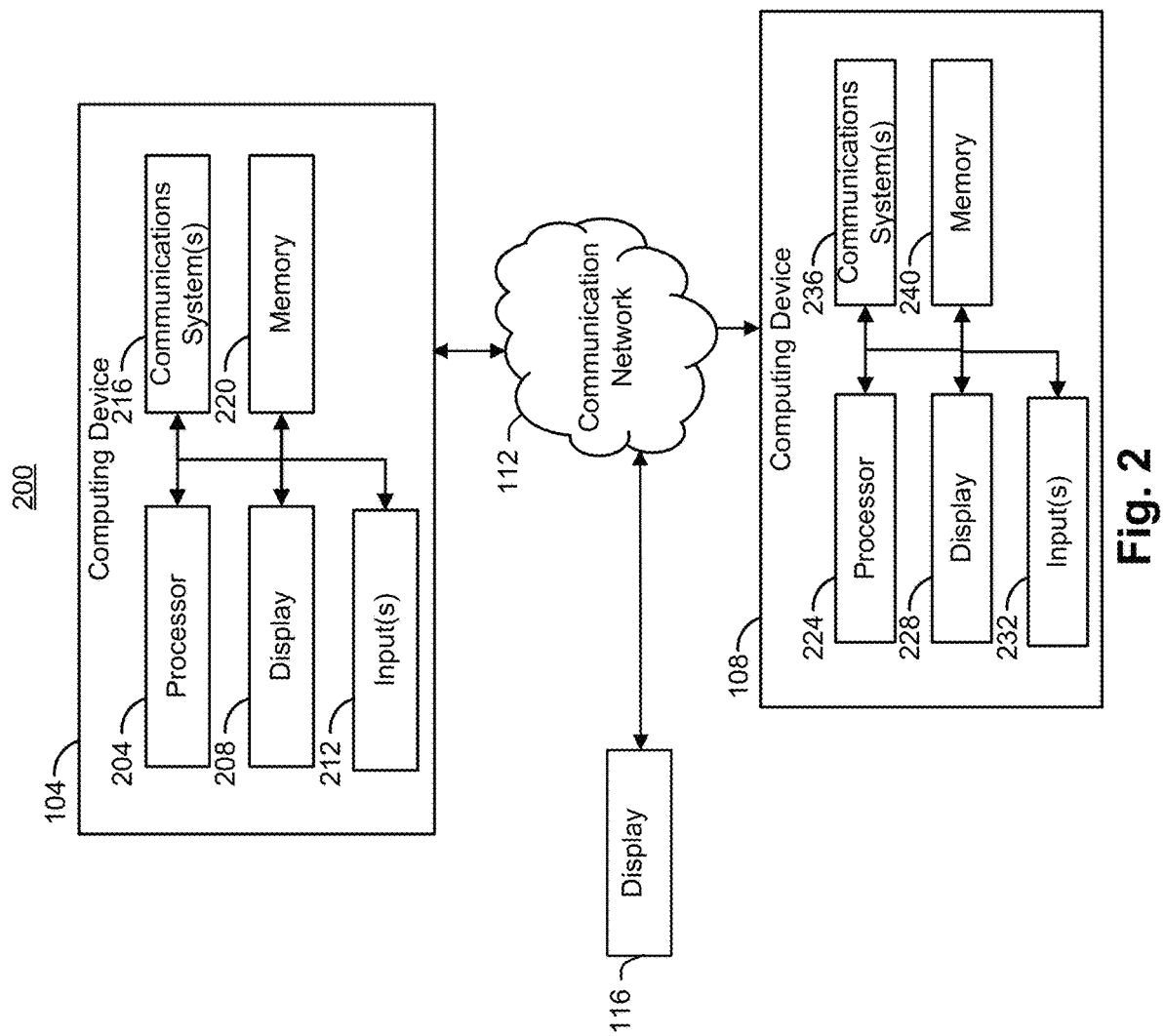
FIG. 2 is an example of hardware that can be used in some embodiments of the system in FIG. 1.

FIG. 2 shows an example 200 of hardware that can be used in some embodiments of the system 100. The computing device 104 can include a processor 204, a display 208, an input 212, a communication system 216, and a memory 220. The processor 204 can be any suitable hardware processor or combination of processors, such as a central processing unit ("CPU"), a graphics processing unit ("GPU"), etc., which can execute a program, which can include the processes described below.

In some embodiments, the display 208 can present a graphical user interface. In some embodiments, the display 208 can be implemented using any suitable display devices, such as a computer monitor, a touchscreen, a television, etc. In some embodiments, the inputs 212 of the computing device 104 can include indicators, sensors, actuatable buttons, a keyboard, a mouse, a graphical user interface, a touch-screen display, etc.

In some embodiments, the communication system 216 can include any suitable hardware, firmware, and/or software for communicating with the other systems, over any suitable communication networks. For example, the communication system 216 can include one or more transceivers, one or more communication chips and/or chip sets, etc. In a more particular example, communication system 216 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 216 allows the computing device 104 to communicate with the secondary computing device 108.

In some embodiments, the memory 220 can include any suitable storage device or devices that can be used to store instructions, values, etc., that can be used, for example, by the processor 204 to present content using display 208, to communicate with the secondary computing device 108 via communications system(s) 216, etc. The memory 220 can include any suitable volatile memory, non-volatile memory, storage, or any suitable combination thereof. For example, the memory 220 can include RAM, ROM, EEPROM, one or more flash drives, one or more hard disks, one or more solid state drives, one or more optical drives, etc. In some embodiments, the memory 220 can have encoded thereon a computer program for controlling operation of computing device 104 (or secondary computing device 108). In such embodiments, the processor 204 can execute at least a portion of the computer program to present content (e.g., user interfaces, images, graphics, tables, reports, etc.), receive content from the secondary computing device 108, transmit information to the secondary computing device 108, etc.

The secondary computing device 108 can include a processor 224, a display 228, an input 232, a communication system 236, and a memory 240. The processor 224 can be any suitable hardware processor or combination of processors, such as a central processing unit ("CPU"), a graphics processing unit ("GPU"), etc., which can execute a program, which can include the processes described below.

In some embodiments, the display 228 can present a graphical user interface. In some embodiments, the display 228 can be implemented using any suitable display devices, such as a computer monitor, a touchscreen, a television, etc. In some embodiments, the inputs 232 of the secondary computing device 108 can include indicators, sensors, actuatable buttons, a keyboard, a mouse, a graphical user interface, a touch-screen display, etc.

In some embodiments, the communication system 236 can include any suitable hardware, firmware, and/or software for communicating with the other systems, over any suitable communication networks. For example, the communication system 236 can include one or more transceivers, one or more communication chips and/or chip sets, etc. In a more particular example, communication system 236 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 236 allows the secondary computing device 108 to communicate with the computing device 104.

In some embodiments, the memory 240 can include any suitable storage device or devices that can be used to store instructions, values, etc., that can be used, for example, by the processor 224 to present content using display 228, to communicate with the computing device 104 via communications system(s) 236, etc. The memory 240 can include any suitable volatile memory, non-volatile memory, storage, or any suitable combination thereof. For example, the memory 240 can include RAM, ROM, EEPROM, one or more flash drives, one or more hard disks, one or more solid state drives, one or more optical drives, etc. In some embodiments, the memory 240 can have encoded thereon a computer program for controlling operation of secondary computing device 108 (or computing device 104). In such embodiments, the processor 224 can execute at least a portion of the computer program to present content (e.g., user interfaces, images, graphics, tables, reports, etc.), receive content from the computing device 104, transmit information to the computing device 104, etc.

The display 116 can be a computer display, a television monitor, a projector, or other suitable displays.

Figure 3:
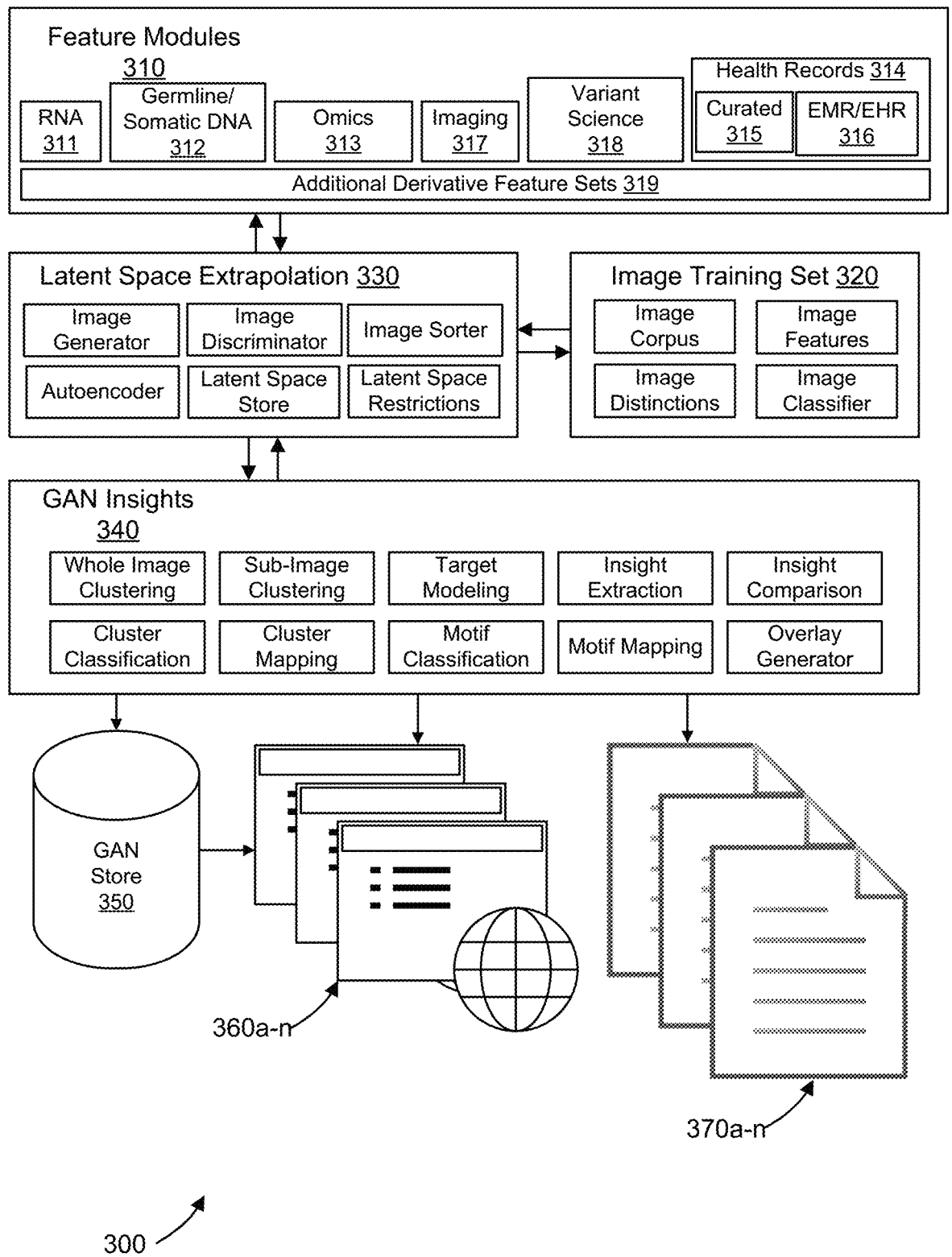
FIG. 3 is an exemplary embodiment of a generative adversarial network (GAN) processing pipeline system.

Referring now to FIG. 3, an exemplary embodiment of a generative adversarial network (GAN) processing pipeline system 300 is shown. The system 300 can include feature modules 310. The feature modules 310 can include an RNA feature module 311, a germline and/or somatic DNA feature module 312, an omics feature module 313, a health record feature module 314, an imaging feature module 317, a variant science feature module 318, and/or an additional derivative feature sets feature module 319. The health records feature module 314 can include a curated records sub-module 315 and/or an electronic medical record (EMR) and/or electronic health record (EHR) sub-module 316.

The feature modules 310 can include a collection of features, or status characteristics, generated for some or all patients whose information is present in the system 300. In some embodiments, the feature modules 310 can include genetic sequencing reports (e.g., from molecular fields), progress reports, testing results, insurance billing codes and/or records, and/or other medical documentation for a patient. Sequencing may include next-generation sequencing (NGS) and may be long-read, short-read, or other forms of sequencing a patient's somatic and/or normal genome. A comprehensive collection of features in additional clinical health records may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from RNA or DNA sequencing, pathology features derived from cellular review by a pathologist, or other imaging.

The system 300 can include an image training set module 320. In some embodiments, the image training set module 320 can include an image corpus (e.g., a collection of object images and/or cell images), image distinctions (e.g., classifications of images), an image classifier (e.g., a model trained to classify images), and/or image features (e.g., one or more patterns and/or motifs that are included in a subset of the image corpus).

The system 300 can include a latent space extrapolation module 330. The latent space extrapolation module 330 can include an image generator (e.g., a generator included in a GAN), an image discriminator (e.g., a discriminator included in a GAN), an image sorter, an autoencoder (e.g., an autoencoder trained to generate latent space representations of raw count data), a latent space store sub-module, and/or a latent space restrictions sub-module.

The system 300 can include a GAN insights module 340. The GAN insights module 340 can include a whole image clustering sub-module, a sub-image clustering sub-module, a target modeling sub-module, an insight extraction sub-module, an insight comparison sub-module, a cluster classification sub-module, a cluster mapping sub-module, a motif classification sub-module, a motif mapping sub-module, and/or an overlay generator. The whole image clustering sub-module and/or a sub-image clustering sub-module can cluster similar images and/or images with similar subsections. The motif classification sub-module and/or the motif mapping sub-module can detect recurring motifs (e.g., a tripartite motif) present in similar images and/or images with similar sub-sections.

In some embodiments, the GAN insights module 340 can communicate with the feature modules 310, the image training set module 320, and the latent space extrapolation module 330 in order to train models, analyze patient data, generate patient images, and/or other tasks. For example, the GAN insights module can train the autoencoder included in the latent space extrapolation module 330 based on RNA count data included in the RNA feature module 311. As another example, the GAN insights module 340 can train the image generator and the image discriminator included in the latent space extrapolation module 330 based on images included in the image corpus included in the image training set module 320. As yet another example, the GAN insights module 340 can cluster images generated based on latent space representations using the image generator included in the latent space extrapolation module 330, and extract insights from the generated images.

The system 300 can include a GAN store 350 that receives trained models (e.g., GANs) and/or data generated by trained models (e.g., insights) included in the GAN insights module 340. In some embodiments, the GAN store 350 can output data generated by the trained models in a structured format for retrieval by a user interface such as a webforms 360a-n included in the system 300. In some embodiments, the GAN insights module 340 can generate and output electronic reports 370a-n for viewing by a remote user (e.g., at a personal computer of a physician).

Figure 4A:
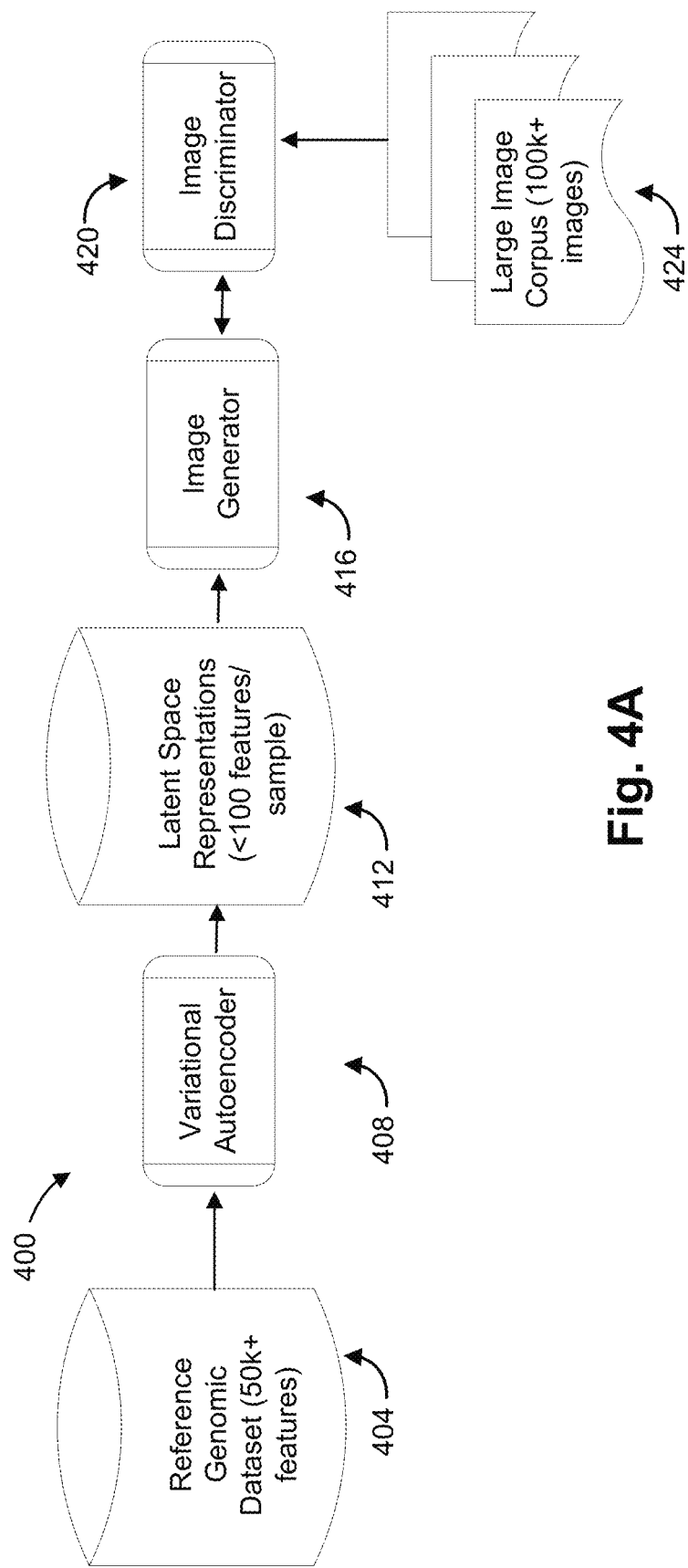
FIG. 4A is an exemplary flow for training a generator to generate an image representative of patient genetic data based on an input latent space representation.

FIG. 4A shows an exemplary flow 400 for training a generator 416 to generate an image representative of patient genetic data based on an input latent space representation. In some embodiments, the generator 416 can include a U-Net convolutional neural network. In some embodiments, the generator 416 can include a pix2pix model. In some embodiments, the generator 416 can be a generative adversarial network (GAN). An exemplary neural network that can be included in the generator 416 is described below in conjunction with FIG. 6. In some embodiments, the generator can include a neural network that can receive a latent space representation included in a latent space representation database 412 and output a single three-channel image (e.g., a 64×64×3 image). In some embodiments, the latent space representation database 412 can include representations having both reduced-dimension genetic data as well as features derived from medical records (e.g., diagnostic information, medical history, genetic data, etc.) as described below in conjunction with FIG. 11B. For example, the patient information can include features derived from imaging data and may further include reports associated with a stained slide, size of tumor, tumor size differentials over time including treatments during the period of change, as well as machine learning approaches for classifying PDL1 status, HLA status, and/or other characteristics from imaging data. The latent space representations can include reduced-dimension genetic data concatenated to at least one value representative of the patient information. For example, a latent space representation can include a latent space representation of genetic data, such as a thirty-two dimension latent space representation of RNA data, and a size of tumor value, which can be a single value, for a total of thirty-three values (i.e., thirty-three dimensions of data).

The flow 400 can include providing genetic data of a number of patients in a genomic dataset 404 to an autoencoder 408 trained to reduce the dimensionality of the genetic data. For example, the genetic data can be RNA read counts including thousands of reads, and the autoencoder 408 can reduce the dimensionality down to less than one hundred dimensions (e.g., a thirty-two dimension image) in a latent space representation. The flow 400 can store the latent space representations generated by the autoencoder 408 in the latent space representation database 412. In some embodiments, the autoencoder 408 can be replaced by other approaches such as principal component analysis (PCA) and/or t-distributed stochastic neighbor embedding (tSNE).

The flow 400 can include a latent space representation, an image generated by the generator 416 based on the latent space representation, and an image included in a set of images 424 provided to a discriminator 420. In some embodiments, the image included in the set of images 424 can be an object image and/or a cell image. In some embodiments, the set of images 424 can include images of abstract and/or mathematical shapes such as polygons, cylinders, fractals, and/or cones, patterns such as hatching patterns, checkerboard patterns, dot patterns, line patterns, and/or herringbone patterns, textures such as gradients, naturally occurring textures (e.g., textures found in granite, limestone, wood, etc.), and/or other patterns, shapes, and/or textures that are identifiable and/or distinguishable by humans. In some embodiments, the set of images 424 can include object images of a plurality of different objects (e.g., an airplane, a bird, a car, a cat, a deer, a dog, a horse, a monkey, a ship, or a truck). For example, in some embodiments, the set of images 424 can include at least a portion of an object image dataset. In some embodiments, the object image dataset can include at least a portion of the STL-10 image dataset, which is available at http://cs.stanford.edu/~acoates/stl10. The STL-10 image dataset includes ten classes of objects including airplane, bird, car, cat, deer, dog, horse, monkey, ship, and truck. The images in the STL-10 dataset are color images sized to 96×96 pixels. For each class of object, there are five hundred training images and eight hundred test images.

The discriminator 420 can learn to differentiate the image included in the set of images 424, which acts as a ground truth, from the image generated by the generator 416 based on the latent space representation. The generator 416 can be trained to make realistic images (e.g., images of objects and/or cells) from the latent space representation, and the discriminator 420 can be trained to represent nuanced information encoded in the images generated by the generator 416. The generator 416 can convert the latent space representations to images while maintaining the general properties of the latent space representations.

In some embodiments, the discriminator 420 can receive an image and output a label ranging from 0 to 1, with 0 indicating that image is generated by the generator 416 and 1 indicating that the image is real (e.g., the ground truth image included in the set of images 424). In some embodiments, the discriminator 420 can be a PatchGAN discriminator, such as a 1×1 PatchGAN discriminator. An exemplary discriminator is described below in conjunction with FIG. 7. The generator 416 and the discriminator 420 can be included in a training model (e.g., a GAN model), and the generator can be used without the discriminator 420 after training.

In some embodiments, the discriminator 420 can output a predicted label (e.g., a "0" or a "1") to an objective function calculation. The predicted label can indicate if an image generated by the generator 416 is "fake" or "real." The objective function calculation can include calculating a loss value using GANLoss, SSIM, L1, and/or Binary Cross Entropy (BCE). The objective function calculation include different loss functions based on what a training goal of the generator 416 and the discriminator is. For example, the objective function calculation can vary based on if the training goal is minimizing false positives and/or false negatives, as well as maximizing true positives and/or true negatives. In the present case, the goal is to train the generator 416 to fool the discriminator 420 while not making each latent space generation too unique, which may diminish grouping generated images during patient analysis. Intermediate training to achieve the goal of training the generator 416 to fool the discriminator 420 while not making each latent space generation too unique will be further discussed below.

In some embodiments, the objective function can be calculated as a weighted sum of GANLoss, SSIM, and L1. In some embodiments, the GANLoss can be calculated based on the predicted label output by the discriminator. The GANLoss can be used to determine whether the artificial generated image is fake or real. In some embodiments, the L1 loss can be calculated based on the generated image and the corresponding ground truth image in the set of images 424. The L1 loss can be used as an additional objective to be minimized to ensure that the generated and the corresponding ground truth image have the least mean absolute error in addition to GANLoss. The objective function can update weights included in the generator 416 and the discriminator 420 based on the objective function calculation.

Certain machine learning models, such as the pix2pix model, may only use GANLoss and L1 loss in training a generator. The objective function calculation can include an SSIM metric in addition to the GANLoss and the L1 loss, which can improve the performance of the generator 416 in comparison to a generator trained using only GANLoss and L1 loss. In some embodiments, the objective function may only use BCE as a loss function.

To train the generator 416 to generate images based on latent space representations as an image, the amount of training may be carefully controlled. Carefully controlling the amount of training of the generator 416 to generate images based on latent space representation enables a balance between images with no discernable patterns and those with patterns that are too unique. For example, with too little training, the generator 416 may generate images that have no discernible patterns (e.g., simple, amorphous hues and colors). Conversely, with too much training, the generator 416 may generate a unique image pattern for each latent space representation. If the patterns for each image are too unique, then grouping (e.g., clustering) of similar patients using images generated by the generator 416 may be more difficult and/or grouping performance may be negatively impacted.

Figure 4B:
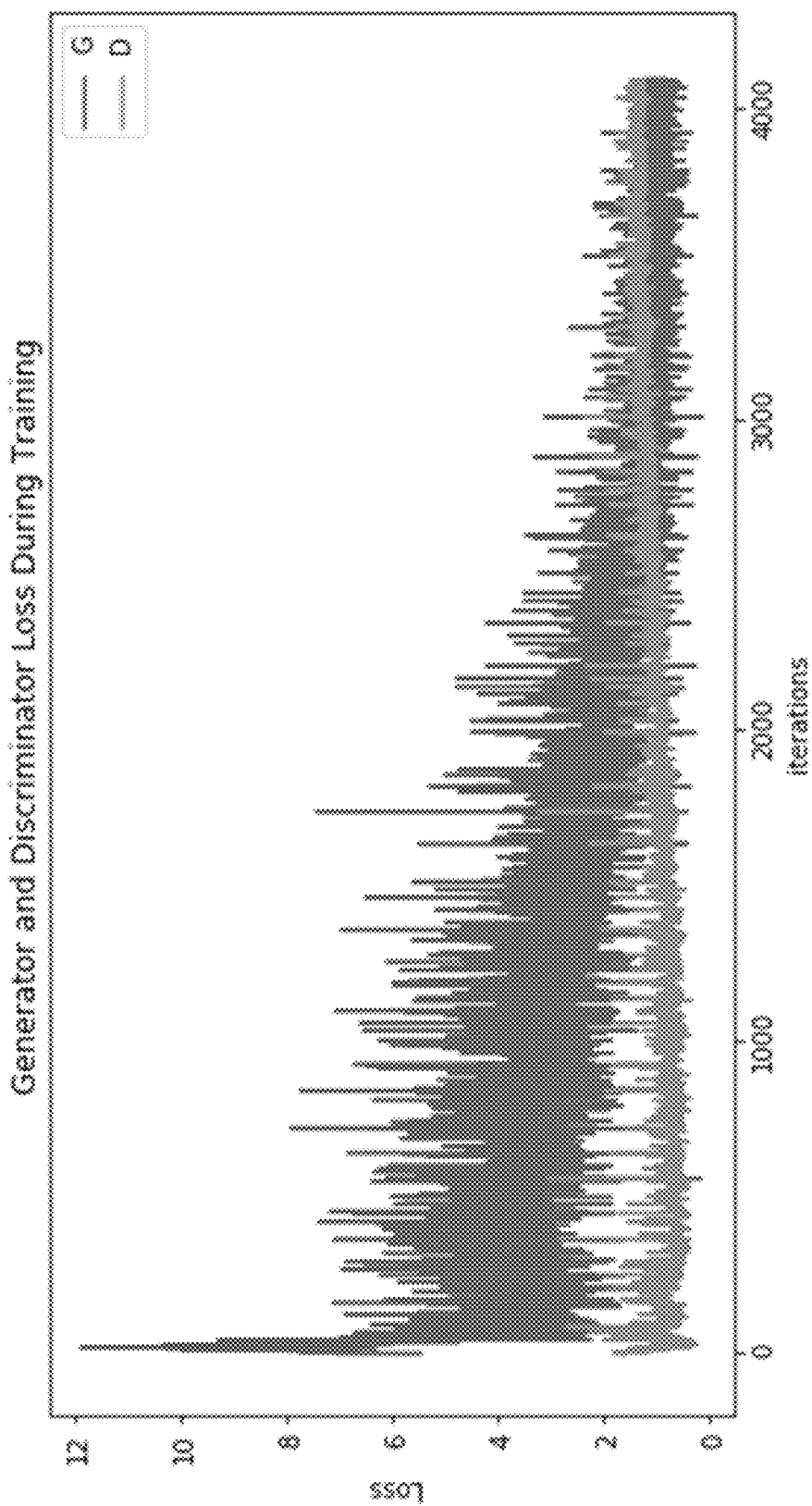
FIG. 4B shows a graph of loss vs. iterations for generator loss and discriminator loss in an overtrained model.
Figure 4C:
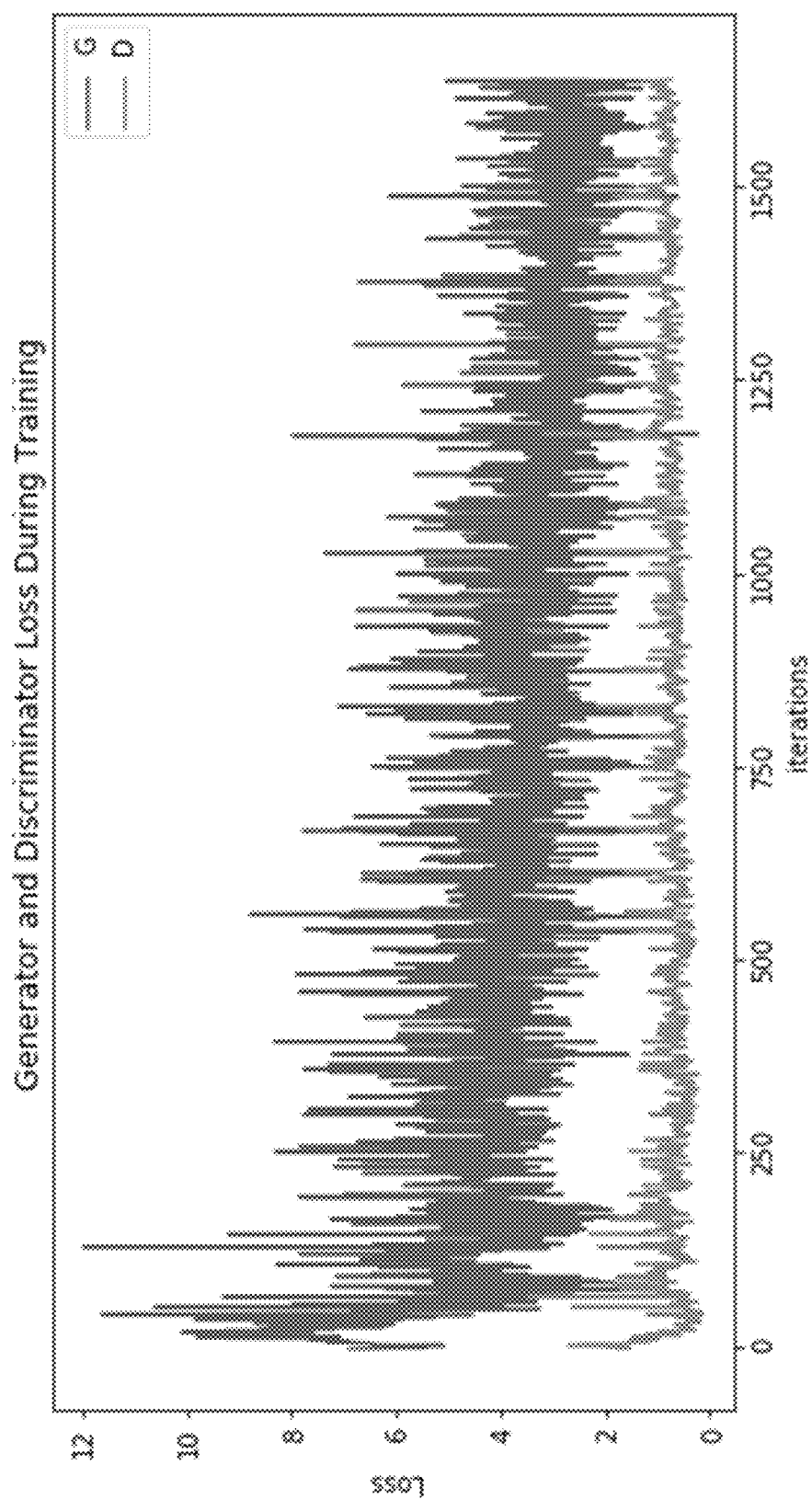
FIG. 4C shows a graph of loss vs. iterations for generator loss and discriminator loss in an intermediately trained model.

Once intermediately trained, the generator 416 can represent latent space representations that are 'close' to one another in the latent space with similar image structures, resulting in generated images that encode meaning with respect to the underlying latent space representation. FIG. 4B shows generator loss and discriminator loss results in training for an overtrained model, where each sample results in a unique image, while FIG. 4C shows generator loss and discriminator loss results in training for an intermediately trained model that produces images with patterns and motifs.

It was found that training time is a function of both the underlying complexity of the latent space and the number of training samples. In some embodiments, intermediately trained generators (e.g., the generator 416) can be trained using about 1500-2000 training RNA samples with four training epochs, which has been shown to produce intermediately trained generators in testing. In some embodiments, the STL-10 image data set can used as the reference image corpus, such that each training epoch includes training across the 105 k images in the STL-10 image dataset and random samples from the latent space. For FIG. 4B, the generator was trained using a training RNA sample set of five hundred over five training epochs. For FIG. 4C, the generator was trained using a training RNA sample set of five hundred over two training epochs.

In FIG. 4B, the generator loss passes below the discriminator loss, which is characteristic of an overtrained model. In FIG. 4C, the generator loss has nearly plateaued while still exhibiting separation from the discriminator loss, which is characteristic of an intermediately trained model. Thus, to train an intermediately trained generator, an appropriate number of samples and training epochs (e.g., five hundred samples and two training epochs) can be chose to keep the generator loss above the discriminator loss for the majority of and/or the entirety of the training.

An intermediately trained generator can be a generator included in a GAN trained with a generator loss remaining above a discriminator loss for the majority of and/or the entirety of the training. As described above, an intermediately trained models preferred to avoid generating images with no discernible patterns due to undertraining, as well as generating, as well as generating images with a unique image pattern for each latent space representation due to overtraining. If images have patterns that are non-discernable and/or too unique, then grouping (e.g., clustering) of similar patients using images generated by the generator 416 may be more difficult and/or grouping performance may be negatively impacted.

Figure 5:
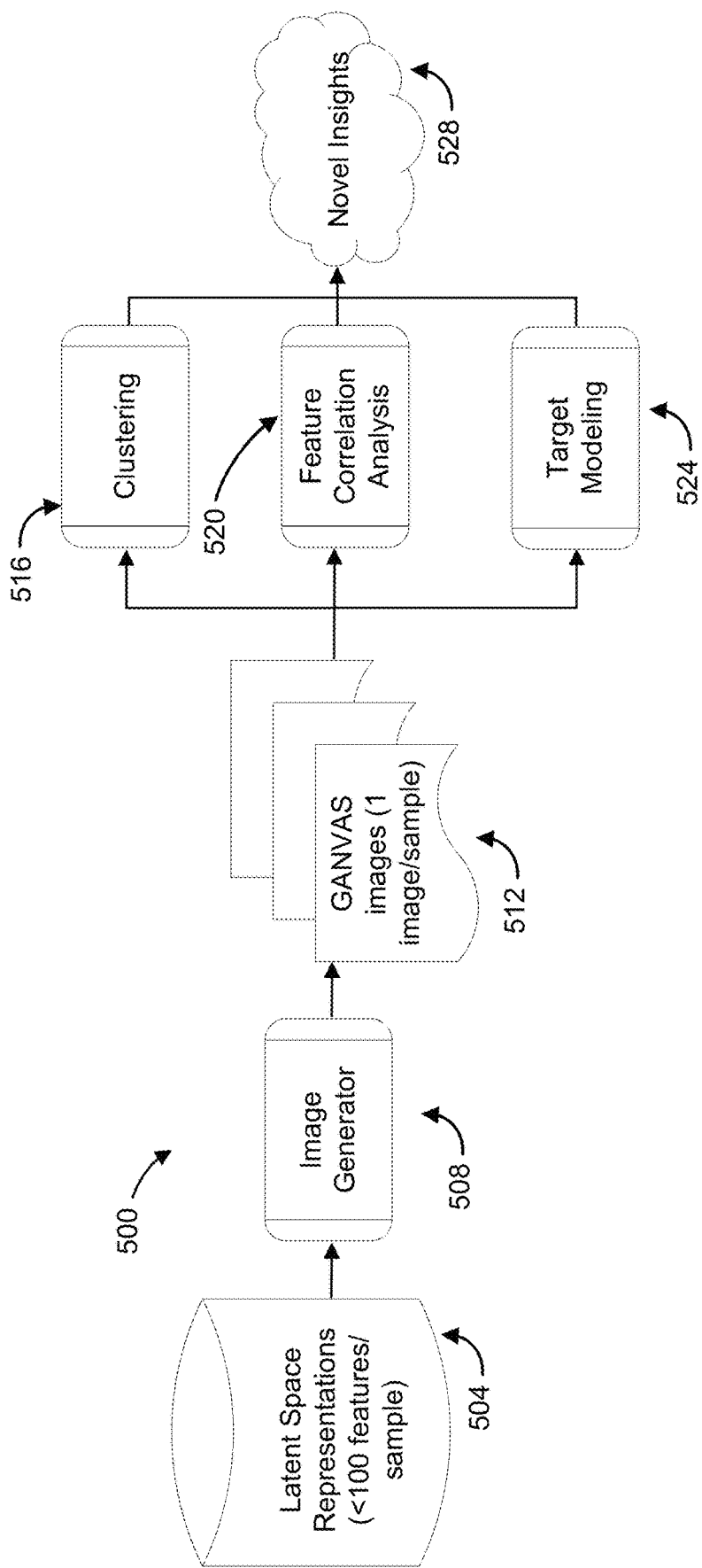
FIG. 5 is an exemplary flow for analyzing a patient.

Referring to FIG. 4A as well as FIG. 5, an exemplary flow 500 for analyzing a patient is shown. The flow 500 can include providing one or more latent space representations included in a latent space representation database 504 to a trained model 508. The trained model 508 can be the generator 416 trained using the flow 400 in FIG. 4A. For each latent space representation, the trained model 508 can generate an image representative of the latent space representation. The image may be referred to as a latent space image. The trained model 508 can generate a number of latent space images 512 that can be used to analyze one or more patients (e.g., diagnose, generate potential treatments, generate cohorts, etc.).

The flow 500 can include analyzing the latent space images 512. The flow 500 can include clustering 516 the latent space images 512, performing feature correlation analysis 520 on the latent space images 512, and/or performing target modeling 524 on the latent space images 524. Data 528 generated by the flow 500 (e.g., clusters, correlation values, etc.) can be output to at least one of a memory (e.g., for storage) and/or to a display (e.g., for viewing by a medical practitioner). The data 528 may also be referred to as insights.

Figure 6:
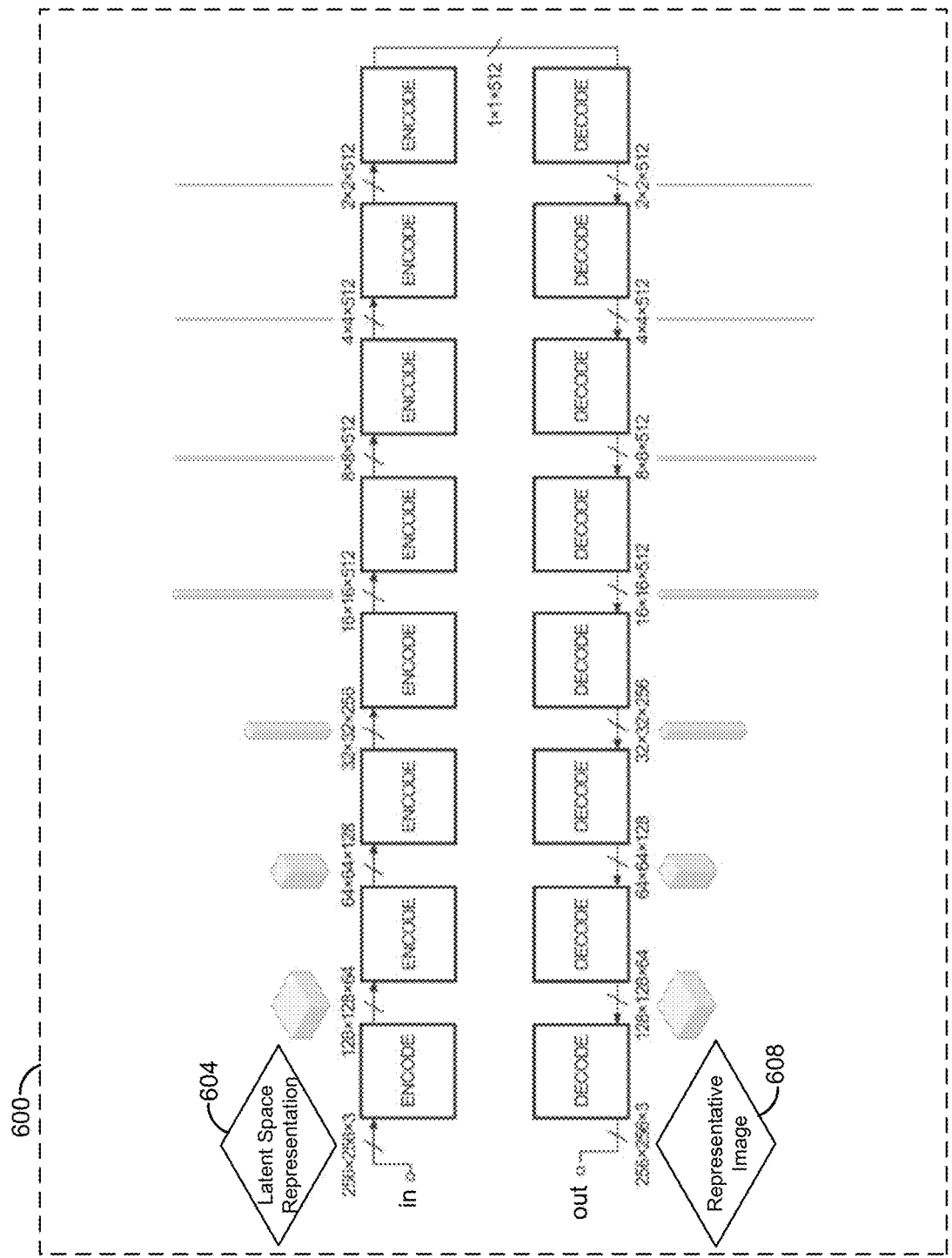
FIG. 6 is an exemplary neural network.

FIG. 6 shows an exemplary neural network 600. The neural network 600 can be trained to receive a latent space representation 604 and generate a representative image 608 based on the latent space representation 604. In some embodiments, the latent space representation 604 can be generated by a trained autoencoder.

In some embodiments, the neural network 600 can include a Unet architecture. In some embodiments, the Unet architecture can be sized to receive a forty dimension input vector and/or array. In some embodiments, the representative image 608 can be a 64×64×3 color image. In some embodiments, the generator 416 in FIG. 4A and/or the trained model 508 in FIG. 5 can include the neural network 600.

Figure 7:
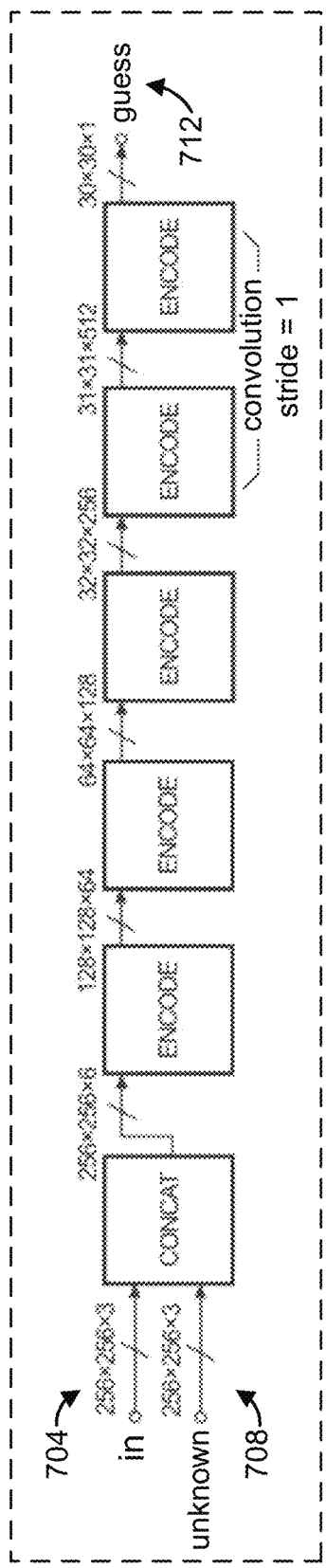
FIG. 7 is an exemplary discriminator.

FIG. 7 shows an exemplary discriminator 700. In some embodiments, the discriminator 700 in FIG. 7 can be included as the discriminator 420 in the flow 400 shown in FIG. 4A. In some embodiments, the discriminator 700 can be a 1×1 PatchGAN. In some embodiments, the discriminator 700 can receive a real-world image 704 from a set of images (e.g., object images and/or cell images) and a representative image 708. In some embodiments, each of the real-world image 704 and the representative image 708 can be 64×64×3 input images. In some embodiments, the real-world image 704 and the representative image 708 can be concatenated. In some embodiments, the concatenated image can be a 64×64×6 input image.

Figure 8:
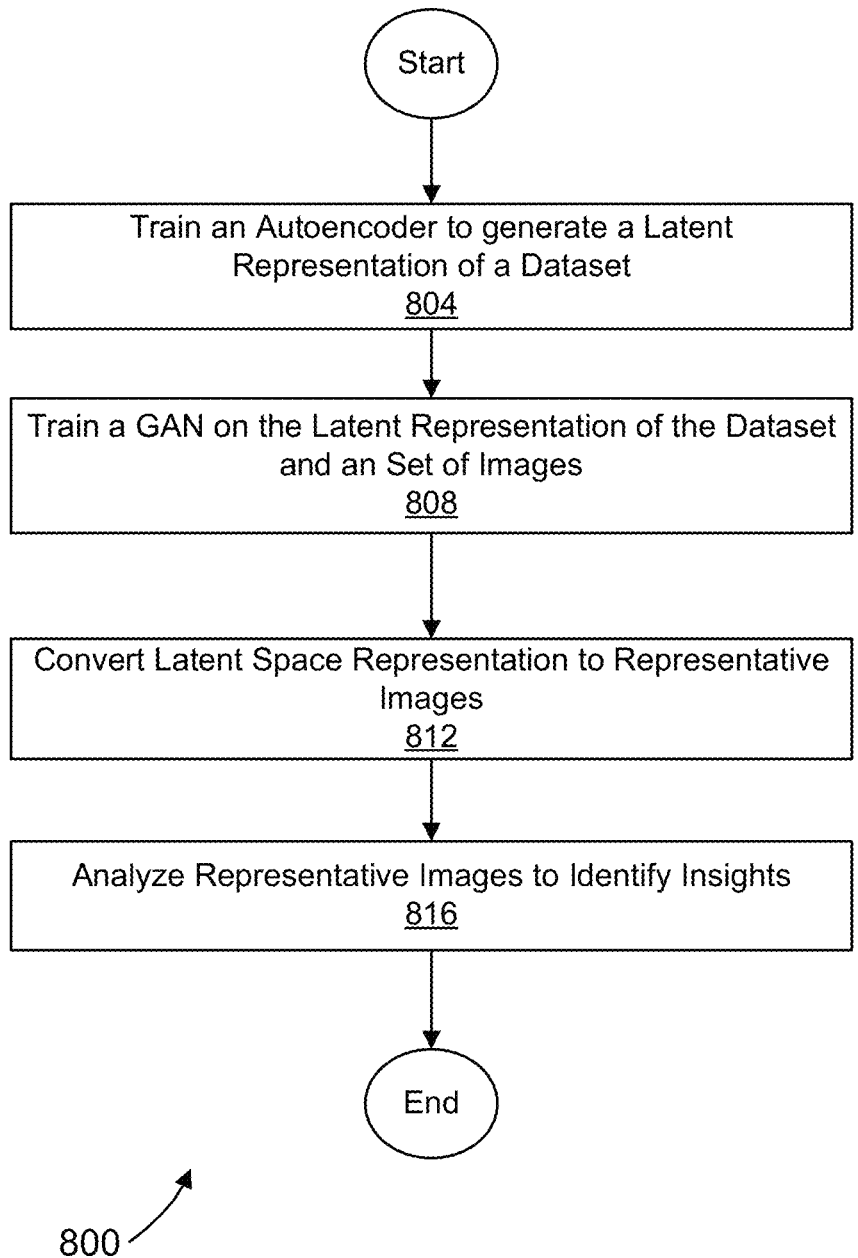
FIG. 8 is an exemplary process that can train a model to generate a representative image of a latent space representation.

In some embodiments, the discriminator 700 can receive the real-world image 704 and the representative image 708 and generate a predicted label 712 indicative of whether or not the representative image 708 is real or fake. In some embodiments, the predicted label 712 can be a "0" to indicate the representative image 708 is fake, and "1" to indicate the representative image 708 is real. In some embodiments, the discriminator 700 can include a neural network FIG. 8 shows an exemplary process 800 that can train a model to generate a representative image of a latent space representation. In some embodiments, the model can be the generator 416 in FIG. 4A, and/or the neural network 600 of FIG. 6. In some embodiments, the model can include a neural network that can receive the latent space representation and output a single three-channel image (e.g., a 64×64×3 image).

The process 800 can be implemented as computer readable instructions on one or more memories or other non-transitory computer readable media, and executed by one or more processors in communication with the one or more memories or other media. In some embodiments, the process 800 can be implemented as computer readable instructions on the memory 220 and/or the memory 240 and executed by the processor 204 and/or the processor 224.

At 804, the process 800 can train an autoencoder to generate a latent space representation of a dataset. In some embodiments, the process 800 can train the autoencoder to generate latent space representations of genomic samples (e.g., RNA samples and/or DNA samples). The genomic samples may include 10,000 or more features. The process 800 can generate a number of latent space representations using the autoencoder.

At 808, the process 800 can train a GAN using the latent space representations of the dataset and a set of images. The set of images can include object images and/or cell images. In some embodiments, the set of images can include at least a portion of the STL-10 image dataset. In some embodiments, the GAN can be intermediately by using an appropriate number of samples and training epochs (e.g., five hundred samples and two training epochs) to keep generator loss above discriminator loss for the majority of and/or the entirety of the training. In some embodiments, the process 800 can train the GAN using the flow 400.

At 812, the process 800 can convert latent space representations to representative images. The process 800 can generate the representative images based on the latent space representations using a trained generator included in the GAN.

At 816, the process 800 can analyze the representative images to identify insights. In some embodiments, the process 800 can generate one or more clusters to identify similar representative images, and by extension, patients. By clustering similar representative images, similar patients can be identified and/or placed into cohorts. Once patients are grouped, the process 800 can identify common and/or recurring characteristics of patients. For example, in some embodiments, the process 800 can identify novel RNA/DNA risk signatures (e.g., genes, genetic pathways, etc.) that contribute to therapy response and/or metastatic risk. In some embodiments, the process 800 can, given a cohort of interest, determine whether there are interesting sub-clusters that exist to define unique properties of patients in the cohort. In some embodiments, the process 800 can, given two cohorts of interest, compare a degree of common sub-clusters and the number of them to speak to how the cohorts are similar/different. In some embodiments, the process 800 can, given a dimensionality reduction technique (e.g., autoencoder, PCA, and/or tSNE), evaluate a quality of the 2D visualization on a full dimensional space. In some embodiments, the process 800 can find high-level interactions from the images directly, and correlate the interactions back to genetic pathways using activation weights included in the generator. In some embodiments, the process 800 can validate pre-existing cohorts for similarity using distance metrics (e.g., L2, L1, etc.). In some embodiments, the process 800 can validate pre-existing clusters. For example, if there are three pre-existing clusters, the process 800 can determine which clusters are actually capturing highly similar, enriched genomic samples with common themes. The process 800 can then end.

Figure 9:
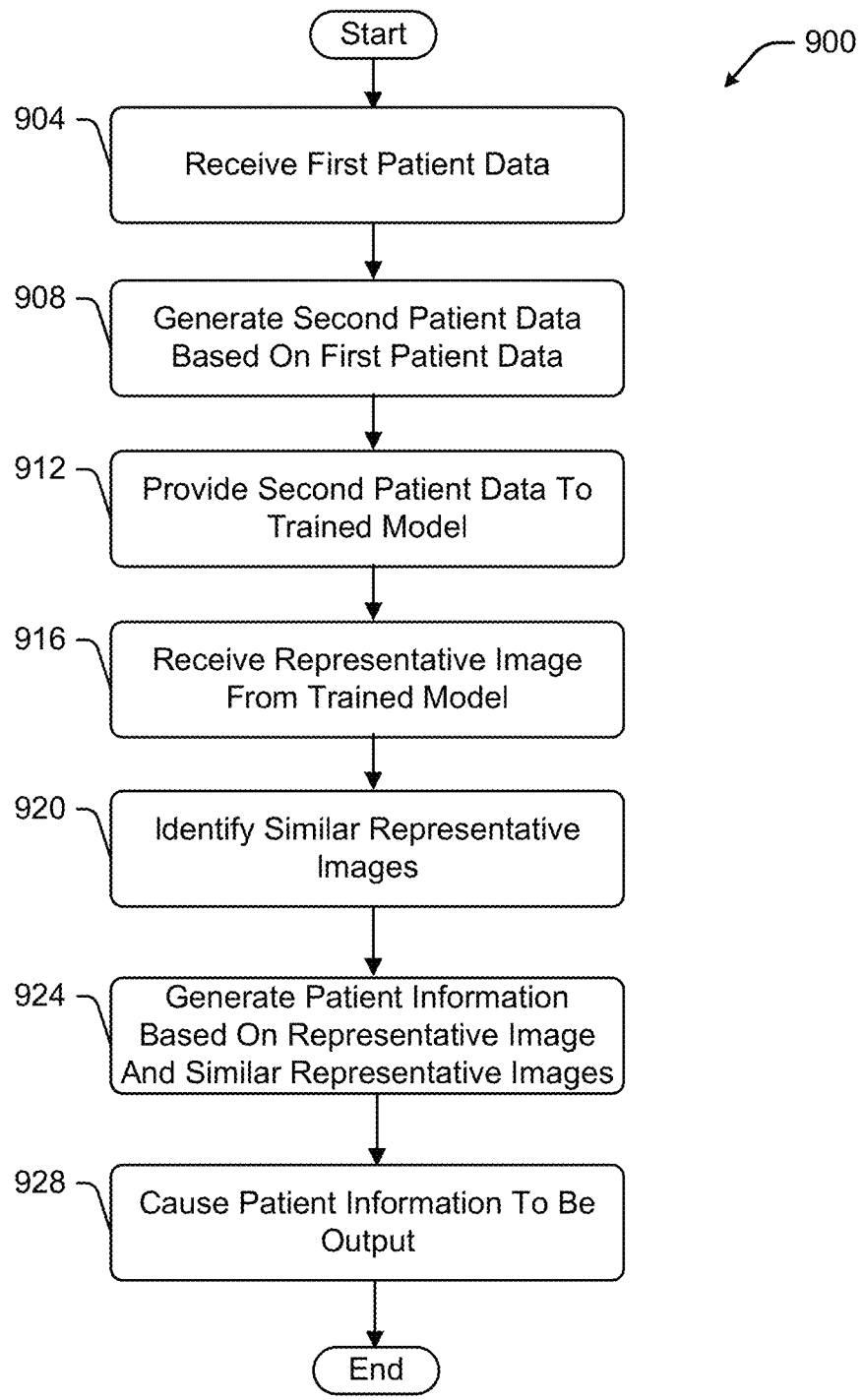
FIG. 9 is an exemplary process that can generate patient information based on representative images.

FIG. 9 shows an exemplary process 900 that can generate patient information based on representative images. More specifically, the process 900 can generate a representative image using a trained model and analyze similar representative images. In some embodiments, the model can be the generator 416 in FIG. 4A, the trained model 508, and/or the neural network 600 in FIG. 6 trained using the process 800. In some embodiments, the model can include a neural network that can receive latent space representations and output a single three-channel image (e.g., a 64×64×3 image).

The process 900 can be implemented as computer readable instructions on one or more memories or other non-transitory computer readable media, and executed by one or more processors in communication with the one or more memories or other media. In some embodiments, the process 900 can be implemented as computer readable instructions on the memory 220 and/or the memory 240 and executed by the processor 204 and/or the processor 224.

At 904, the process 900 can receive first patient data. In some embodiments, the first patient data can include genetic data such as RNA data (e.g., RNA counts) and/or DNA data (e.g., DNA counts). In some embodiments, the patient data can include features derived from medical records (e.g., diagnostic information, medical history, genetic data, etc.) as described below in conjunction with FIG. 11B. For example, the patient information can include features derived from imaging data and may further include reports associated with a stained slide, size of tumor, tumor size differentials over time including treatments during the period of change, as well as machine learning approaches for classifying PDL1 status, HLA status, and/or other characteristics from imaging data. The first patient data can be associated with a patient. In some embodiments, the first patient data can include at least one thousand RNA expression levels.

At 908, the process 900 can generate second patient data based on the first patient data. In some embodiments, the second patient data can be generated based on genetic data such as RNA data (e.g., RNA counts) and/or DNA data (e.g., DNA counts). The second patient data can include a latent space representation of the genetic data. The second patient data can have a lower dimensionality than the first patient data. In some embodiments, the second patient data can include no more than one hundred dimensions of values. In some embodiments, the second patient data can be generated based on the genetic data using a trained autoencoder (e.g., the variational autoencoder 408 in FIG. 4A). In some embodiments, the second patient data can be generated using PCA and/or tSNE. In some embodiments, the second patient data can be generated based on genetic data and at least one other feature included in the patient data. For example, the second patient data can include a latent space representation of the genetic data, such as a thirty-two dimension latent space representation, and a size of tumor value, which can be a single value, for a total of thirty-three values.

At 912, the process 900 can provide the second patient data to a trained model. In some embodiments, the trained model can include generator 416 in FIG. 4A, the trained model 508 in FIG. 5, and/or the neural network 600 in FIG. 6.

At 916, the process 900 can receive a representative image from the trained model. The representative image can represent data included in the latent space representation and/or any other patient data included in the second patient data. The representative image can be referred to as a patient image.

At 920, the process 900 can identify similar representative images. Each image included in the similar representative images can be associated with a patient included in a group of patients. In some embodiments, the process 800 can cluster the representative image with a subset of images included in a set of images generated by the trained model. In this way, a cohort of patients similar to the patient can be identified. In some embodiments, the process 900 can identify a pattern in the patient image that is present in at least one other image in the set of images generated by the trained model. Some images may have recurring motifs, such as a tripartite motif, that are not captured by typical dimensionality reduction techniques such as t-SNE. Thus, in some embodiments, the process 900 can identify a pattern in the patient image that is present in at least one other image in a set of images generated by the trained model.

At 924, the process 900 can generate patient information based on the representative image and the similar representative images. In some embodiments, the process 900 can provide the patient image and the similar representative images to an insights engine and/or analysis engine to generate diagnostic metrics that can be used in treating the patient (e.g., prescribing treatment, identifying compatible trials, etc.) and/or identifying common traits of the patient and the patients associated with the similar representative images. In some embodiments, the at least one diagnostic metric can include a gene variant present in the patient and at least a portion of the group of patients, a disease present in the patient and at least a portion of the group of patients, a preexisting condition present in the patient and at least a portion of the group of patients, a treatment provided to at least a portion of the group of patients, or a trial participated in by at least a portion of the group of patients. In some embodiments, the patient information can include a potential treatment for the patient. In some embodiments, the patient information can include the group of patients associated with the similar representative images. The group of patients may be referred to as a cohort.

In some embodiments, the patient information can include an interactive mapping of patients generated based on the representative image and the similar representative images. In some embodiments, the interactive mapping of patients can include a map (e.g., a two-dimensional graph, a three-dimensional graph, etc.) of the patients associated with representative image and the similar representative images. In some embodiments, the mapping can include, for each patient, a patient identifier (e.g., a patient ID), a color coding identifying a group the patient belongs to, and/or supplemental information about the patient such as a gene variant present in the patient, a disease the patient has and/or has had, a preexisting condition of the patient, a treatment provided to the patient, a trial participated in by the patient in, and/or other relevant patient information. In some embodiments, the supplemental information can include the patient information received at 904. In some embodiments, at least the supplemental information can be selectively hidden (e.g., only displayed when the user selects a given patient). In some embodiments, the mapping can identify similar patients and/or allow a user to move patients between grouping (e.g., clusters) and/or verify patients are similar based on generated images associated with the patients. In some embodiments, the mapping can include a Venn diagram of the patients and/or predetermined groups of the patients that have been generated previously (e.g., clusters generated based on latent space generations). An example of an interactive mapping is described below in conjunction with FIGS. 10A-10B.

At 928, the process 900 can cause the patient information to be output. In some embodiments, the process 900 can cause the patient information to be output to at least one of a memory (e.g., the memory 220 and/or the memory 240) and/or a display (e.g., the display 116, the display 208, and/or the display 228). The process 900 can then end.

Figure 10A:
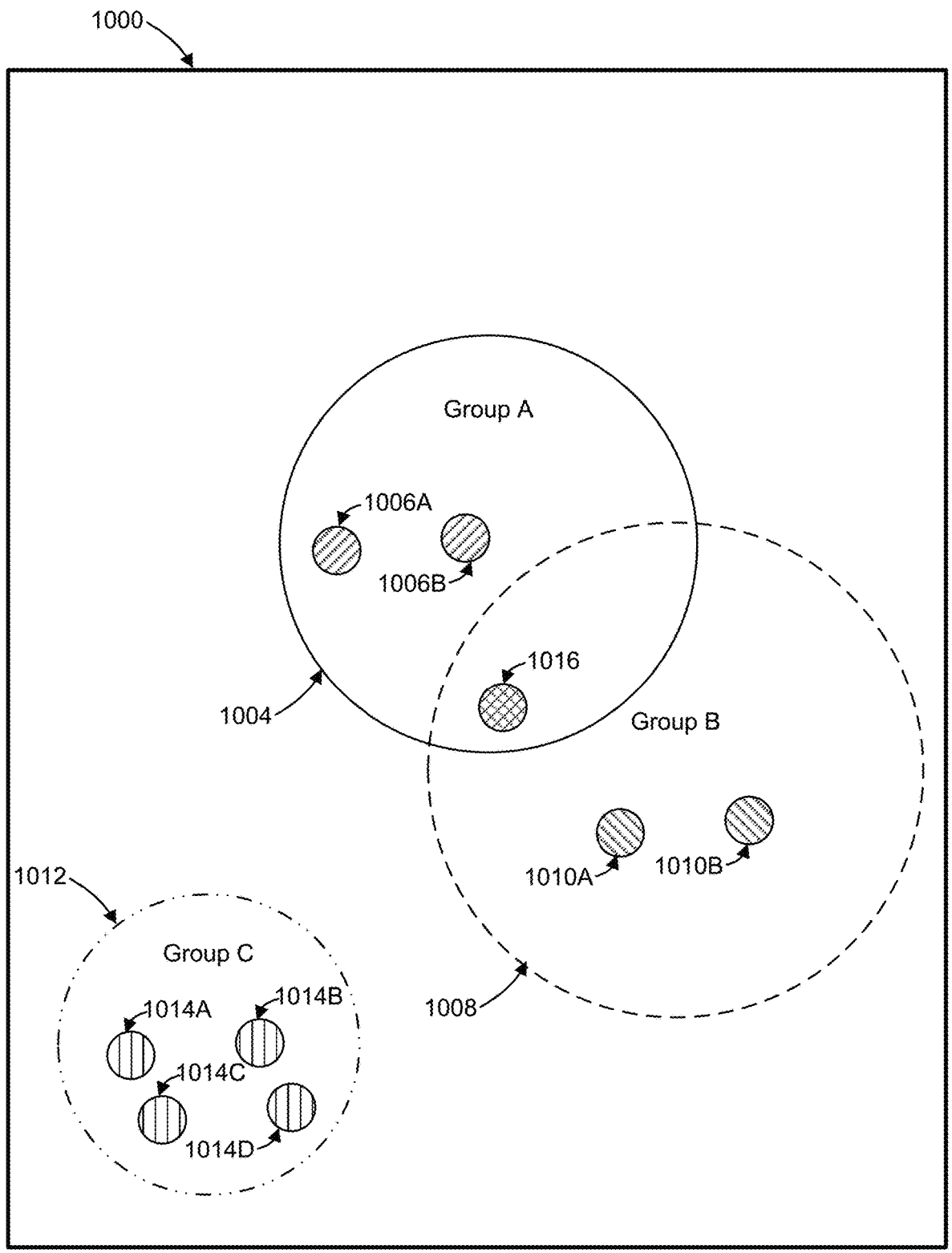
FIG. 10A is an exemplary graphical user interface (GUI) for displaying a plurality of patients associated with generated images.

FIG. 10A shows an exemplary graphical user interface (GUI) 1000 for displaying a plurality of patients associated with generated images (e.g., images generated by the trained model 508). The GUI 1000 can include a plurality of groups. In some embodiments, the plurality of groups can include a first group 1004, a second group 1008, and a third group 1012. Each group can include one or more patients included in a set of patients. For example, the first group 1004 can include a first patient 1006A and a second patient 1006B, the second group 1008 can include a third patient 1010A and a fourth patient 1010B, and the third group 1012 can include a fifth patient 1014A, a sixth patient 1014B, a seventh patient 1014C, and an eighth patient 1014D. In some embodiments, the groups can be generated based on latent space representations associated with patients included in the set of patients. For example, the groups 1004, 1008, 1012 can be generated using clustering (e.g., k-means clustering) on the latent space generations.

In some embodiments, to aid in providing visual differentiation, the groups 1004, 1008, 1012 can be different colors, different shading, and/or have different line patterns. Additionally or alternatively, the patients included in the groups 1004, 1008, 1012 can be different colors, different shading, and/or have different line patterns.

Figure 10B:
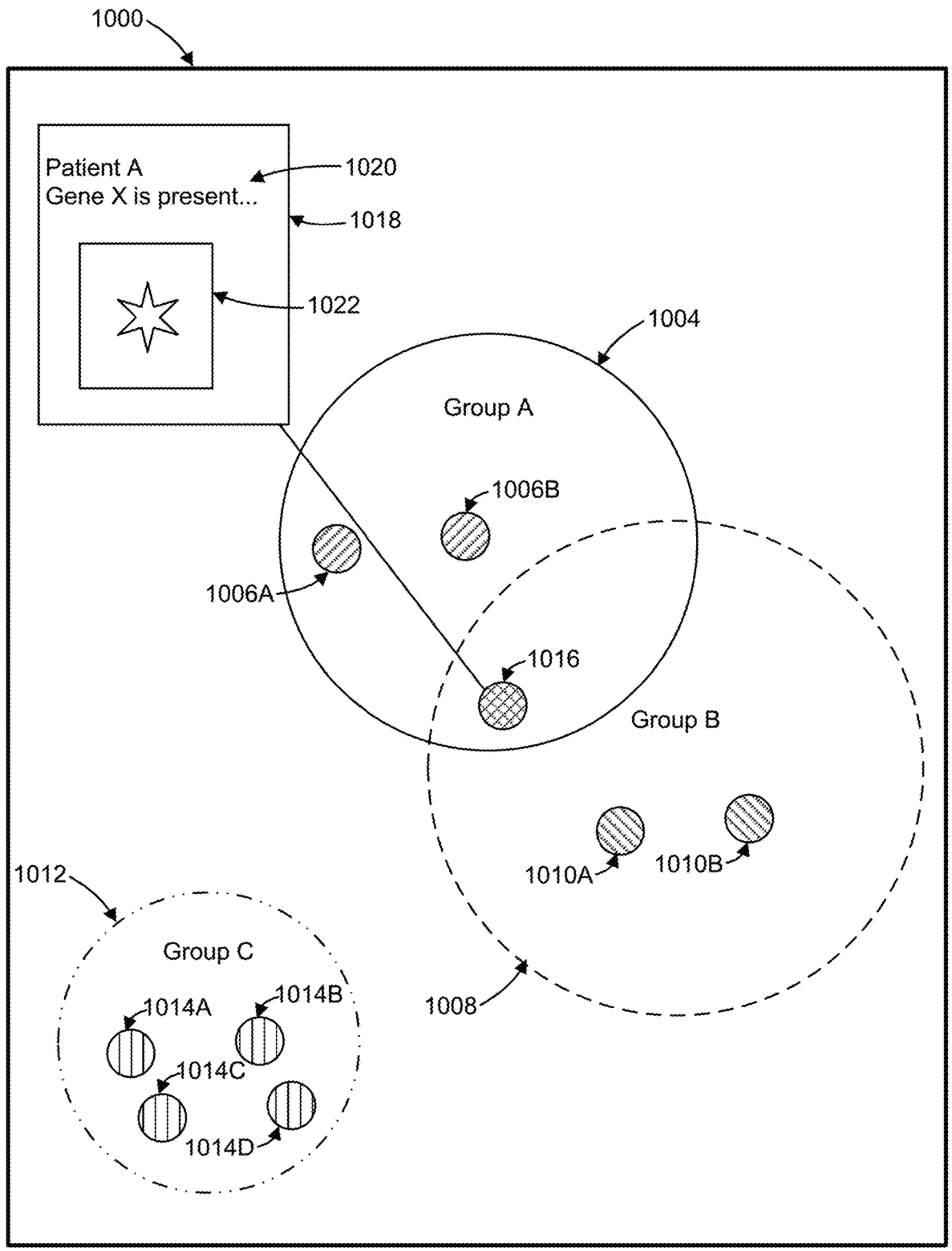
FIG. 10B is another view of the exemplary GUI in FIG. 10A.

Referring now to FIGS. 10A and 10B, the GUI 1000 can provide supplemental information about each patient. In some embodiments, the GUI 1000 can selectively provide a visual indicator 1018 (e.g., a pop-up window) to a user. For example, the GUI 1000 can provide a visual indicator 1018 in response to a cursor being hovered over the patient. As shown, the visual indicator 1018 can be displayed for a ninth patient 1016. The visual indicator 1018 can include patient information 1020 about ninth patient 1016 (e.g., presence of a Gene X) and/or a generated image 1022. The generated image 1022 can be generated using a trained generator (e.g., the trained model 508). A user can verify that the groups 1004, 1008, 1012 include similar patients using the generated image 1022. For example, if the ninth patient 1016 is placed into the first group 1004, the user can verify that the placement is correct. The user can view the generated image and discern a six-point star motif. The user can then compare generated image 1022 to generated images associated with patients in the first group 1004 as well as the second group 1008, which has "nearby" patients. The user may discover that the star motif is more common in generated images associated with patients in the second group 1008 (e.g., generated images associated with the third patient 1010A and the fourth patient 1010B have the star motif) and none of the generated images associated with patients in the first group 1004 have the motif (e.g., generated images associated with the first patient 1006A and the second patient 1006B do not have the star motif). The user can then move the ninth patient 1016 from the first group 1004 to the second group 1008. In some embodiments, a clustering algorithm can place the ninth patient 1016 into both the first group 1004 and the second group 1008 if the ninth patient 1016 is "close" enough to both groups (e.g., the difference in the distance to the first group 1004 and the distance to the second group 1008 is less than a predetermined threshold). In these embodiments, the first group 1004 and the second group 1008 can be displayed as overlapping in Venn diagram fashion. Additionally and/or alternatively, the ninth patient 1016 can be displayed as having a unique pattern and/or color different from the patterns and/or colors used for patients in the first group 1004 and the second group 1008. In some embodiments, the unique pattern and/or color can be a blend of the patterns and/or colors of the patients in the first group 1004 and the second group 1008 (e.g., left diagonal and right diagonal patterns are blended to a left/right double diagonal pattern, blue and red colors are blended to purple, etc.).

FIG. 11A shows a sample breast cancer ductal carcinoma in situ (DCIS) H & E slide, an example of a relatively benign tumor. FIG. 11B shows exemplary patient data. FIG. 11C shows an exemplary latent space representation of RNA. The RNA can be sequenced to produce counts for about 20,000 genes, which are then encoded in a latent space representation having a predetermined dimensionality (e.g., thirty-two dimensions for certain variational autoencoders) using a variational autoencoder (VAE). FIG. 11D shows an image generated using a trained model (e.g., the trained model 508 in FIG. 5) based on the latent space representation in FIG. 11C. It is noted that the undifferentiated nature of the tumor could be a cause of a lack of concrete patterns in the generated image in FIG. 11D.

The patient data in FIG. 11B can include a collection of features associated with a patient. The features can be generated by one or more modules as described below. Feature collections may include a diverse set of fields available within patient health records. Clinical information may be based upon fields which have been entered into an electronic medical record (EMR) or an electronic health record (EHR) by a physician, nurse, or other medical professional or representative. Other clinical information may be curated from other sources, such as molecular fields from genetic sequencing reports. Sequencing may include next-generation sequencing (NGS) and may be long-read, short-read, or other forms of sequencing a patient's somatic and/or normal genome. A comprehensive collection of features in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from an RNA feature module or a DNA feature module sequencing.

Another subset of features, imaging features from an imaging feature module, may comprise features identified through review of a specimen, for example, through pathologist review, such as a review of stained H & E or IHC slides. As another example, a subset of features may comprise derivative features obtained from the analysis of the individual and combined results of such feature sets. Features derived from DNA and RNA sequencing may include genetic variants from a variant science module which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden (TMB), or other structural variations within the DNA and RNA. Analysis of slides for H & E staining or IHC staining may reveal features such as tumor infiltration, programmed death-ligand 1 (PD-L1) status, human leukocyte antigen (HLA) status, or other immunological features.

Features derived from structured, curated, or electronic medical or health records may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/ statuses, or corresponding dates to any of the above.

Features may be derived from information from additional medical or research based Omics fields including proteomics, transcriptomics, epigenomics, metabolomics, microbiomics, and other multi-omic fields. Features derived from an organoid modeling lab may include the DNA and RNA sequencing information germane to each organoid and results from treatments applied to those organoids. Features derived from imaging data may further include reports associated with a stained slide, size of tumor, tumor size differentials over time including treatments during the period of change, as well as machine learning approaches for classifying PDL1 status, HLA status, or other characteristics from imaging data. Other features may include the additional derivative features sets from other machine learning approaches based at least in part on combinations of any new features and/or those listed above. For example, imaging results may need to be combined with MSI calculations derived from RNA expressions to determine additional further imaging features. In another example a machine learning model may generate a likelihood that a patient's cancer will metastasize to a particular organ or any other organ. Other features that may be extracted from medical information may also be used. There are many thousands of features, and the above listing of types of features are merely representative and should not be construed as a complete listing of features.

An alterations module may be one or more microservices, servers, scripts, or other executable algorithms which generate alteration features associated with de-identified patient features from the feature collection. Alterations modules may retrieve inputs from the feature collection and may provide alterations for storage. Exemplary alterations modules may include one or more of the following alterations as a collection of alteration modules.

An IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction in immunoperoxidase staining. Alternatively, the antibody can also be tagged to a fluorophore, such as fluorescein or rhodamine in immunofluorescence. Approximations from RNA expression data, H & E slide imaging data, or other data may be generated.

A Therapies module may identify differences in cancer cells (or other cells near them) that help them grow and thrive and drugs that "target" these differences. Treatment with these drugs is called targeted therapy. For example, many targeted drugs are lethal to the cancer cells with inner 'programming' that makes them different from normal, healthy cells, while not affecting most healthy cells. Targeted drugs may block or turn off chemical signals that tell the cancer cell to grow and divide rapidly; change proteins within the cancer cells so the cancer cells die; stop making new blood vessels to feed the cancer cells; trigger a patient's immune system to kill the cancer cells; or carry toxins to the cancer cells to kill them, without affecting normal cells. Some targeted drugs are more "targeted" than others. Some might target only a single change in cancer cells, while others can affect several different changes. Others boost the way a patient's body fights the cancer cells. This can affect where these drugs work and what side effects they cause. Matching targeted therapies may include identifying the therapy targets in the patients and satisfying any other inclusion or exclusion criteria that might identify a patient for whom a therapy may be effective.

A Trial module may identify and test hypotheses for treating cancers having specific characteristics by matching features of a patient to clinical trials. These trials have inclusion and exclusion criteria that may be matched to enroll a patient and which may be ingested and structured from publications, trial reports, or other documentation.

An Amplifications module may identify genes which increase in count (for example, the number of gene products present in a specimen) disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another.

An Isoforms module may identify alternative splicing (AS), the biological process in which more than one mRNA type (isoform) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as the number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternatively spliced isoforms.

A SNP (single-nucleotide polymorphism) module may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underlie differences in human susceptibility to a wide range of diseases (e.g. -sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome.

An Indels module may identify an insertion or deletion of bases in the genome of an organism classified among small genetic variations. While indels usually measure from 1 to 10,000 base pairs in length, a microindel is defined as an indel that results in a net change of 1 to 50 nucleotides. Indels can be contrasted with a SNP or point mutation. An indel inserts and/or deletes nucleotides from a sequence, while a point mutation is a form of substitution that replaces one of the nucleotides without changing the overall number in the DNA. Indels, being insertions and/or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites.

An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication, which causes the cells to accumulate errors in their DNA. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs).

A TMB (tumor mutational burden) module may identify a measurement of mutations carried by tumor cells and is a predictive biomarker being studied to evaluate its association with response to Immuno-Oncology (1-0) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials.

A CNV (copy number variation) module may identify deviations from the normal genome, especially in the number of copies of a gene, portions of a gene, or other portions of a genome not defined by a gene, and any subsequent implications from analyzing genes, variants, alleles, or sequences of nucleotides. CNV are the phenomenon in which structural variations may occur in sections of nucleotides, or base pairs, which include repetitions, deletions, or inversions.

A Fusions module may identify hybrid genes formed from two previously separate genes. It can occur as a result of: translocation, interstitial deletion, or chromosomal inversion. Gene fusion can play an important role in tumorigenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

A VUS (variant of unknown significance) module may identify variants which are detected in the genome of a patient (especially in a patient's cancer specimen) but cannot be classified as pathogenic or benign at the time of detection. VUS may be catalogued from publications to identify if they may be classified as benign or pathogenic.

A DNA Repair Pathways module (for example, a pathway engine 200n) may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations.

A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant classification may include evaluating features from the feature collection, alterations from the alteration module, and other classifications from within itself from one or more classification modules. Structural variant classification may provide classifications to a stored classifications storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference dataset's mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules. A classifier for clinical trials may include evaluation of variants identified from the alteration module which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, tumor mutational burden, indels, SNP, MNP, fusions, and other alterations which may be classified based upon the results of the alteration modules.

Each of the feature collection, alteration module(s), structural variant and feature store may be communicatively coupled to a data bus to transfer data between each module for processing and/or storage. In some embodiments, each of the feature collection, alteration module(s), structural variant and feature store may be communicatively coupled to each other for independent communication without sharing the data bus.

In addition to the above features and enumerated modules, feature modules may further include one or more of the following modules within their respective modules as a sub-module or as a standalone module.

Germline/somatic DNA feature module may comprise a feature collection associated with the DNA-derived information of a patient or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module may comprise a feature collection associated with the RNA-derived information of a patient, such as transcriptome information. These features may include raw sequencing results, transcriptome expressions, genes, mutations, variant calls, and variant characterizations.

A metadata module may comprise a feature collection associated with the human genome, protein structures and their effects, such as changes in energy stability based on a protein structure.

A clinical module may comprise a feature collection associated with information derived from clinical records of a patient and records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken. For cancer(s), the information may include tissue of origin, six month/year survival, recurrence after diagnosis, and/or tissue of unknown origin data.

An imaging module may comprise a feature collection associated with information derived from imaging records of a patient. Imaging records may include H & E slides, IHC slides, radiology images, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway disruptions, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as epigenome module from Omics, may comprise a feature collection associated with information derived from DNA modifications which are not changes to the DNA sequence and regulate the gene expression. These modifications are frequently the result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as microbiome module from Omics, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as proteome module from Omics, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) may also be included in Omics, such as a feature collection associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous image sequence, or video, can be interpreted as the capture of a single image evolving through time of mutations revealing patient insights.

A sufficiently robust collection of features may include all of the features disclosed above; however, models and predictions based from the available features may include models which are trained from a selection of features that are much more limiting than the exhaustive feature set. Such a constrained feature set may include as few as tens to hundreds of features. For example, a model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

A feature store may enhance a patient's feature set through the application of machine learning and analytics by selecting from any features, alterations, or calculated output derived from the patient's features or alterations to those features. Such a feature store may generate new features from the original features found in feature module or may identify and store important insights or analysis based upon the features. The selections of features may be based upon an alteration or calculation to be generated, and may include the calculation of single or multiple nucleotide polymorphisms insertion or deletions of the genome, a tumor mutational burden, a microsatellite instability, a copy number variation, a fusion, or other such calculations. An exemplary output of an alteration or calculation generated which may inform future alterations or calculations includes a finding of lung cancer and variants in EGFR, an epidermal growth factor receptor gene that is mutated in ~10% of non-small cell lung cancer and ~50% of lung cancers from non-smokers. Wherein previously classified variants may be identified in the patient's genome which may inform the classification of novel variants or indicate a further risk of disease. An exemplary approach may include the enrichment of variants and their respective classifications to identify a region nearby or with evidence to interact with EGFR and associated with cancer. Any novel variants detected from a patient's sequencing localized to this region or interactions with this region would increase the patient's risk. Features which may be utilized in such an alteration detection include the structure of EGFR and classification of variants therein. A model which focuses on enrichment may isolate such variants.

The above referenced models may be implemented as artificial intelligence engines and may include gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

Collectively, FIGS. 11A-D form an analytical pathway that can be used to analyze a patient. Using the sample in FIG. 11A, the patient data in FIG. 11B, and/or the latent space representation in FIG. 11C, the image in FIG. 11D can be generated. The image in FIG. 11D can be used to find patients with similar RNA profiles, which may assist a medical practitioner in diagnosing and/or treating the patient. The patient data in FIG. 11B can include previously generated information and/or patient medical history. An oncologist, for example, may review the patient data for a group of patients identified as similar to the patient. In some embodiments, the group of patients can be generated by clustering latent space representation, which can then be verified by humans viewing generated images (e.g., the image in FIG. 11C) associated with the latent space representations.

Figure 12B:
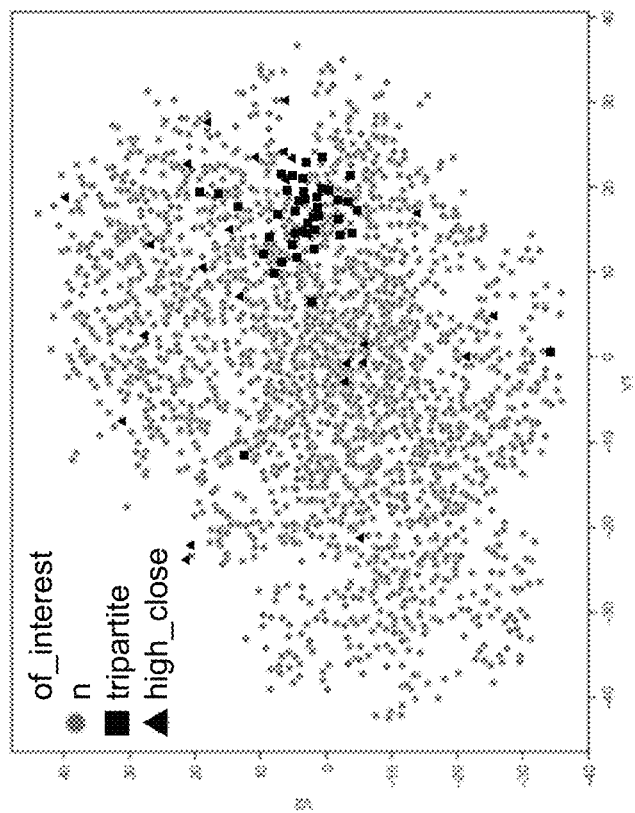
FIG. 12B is a two-dimensional t-SNE projection of a cohort of non-small-cell lung carcinoma (NSCLC) RNA samples encoded through a variational autoencoder (VAE).
Figure 12A:
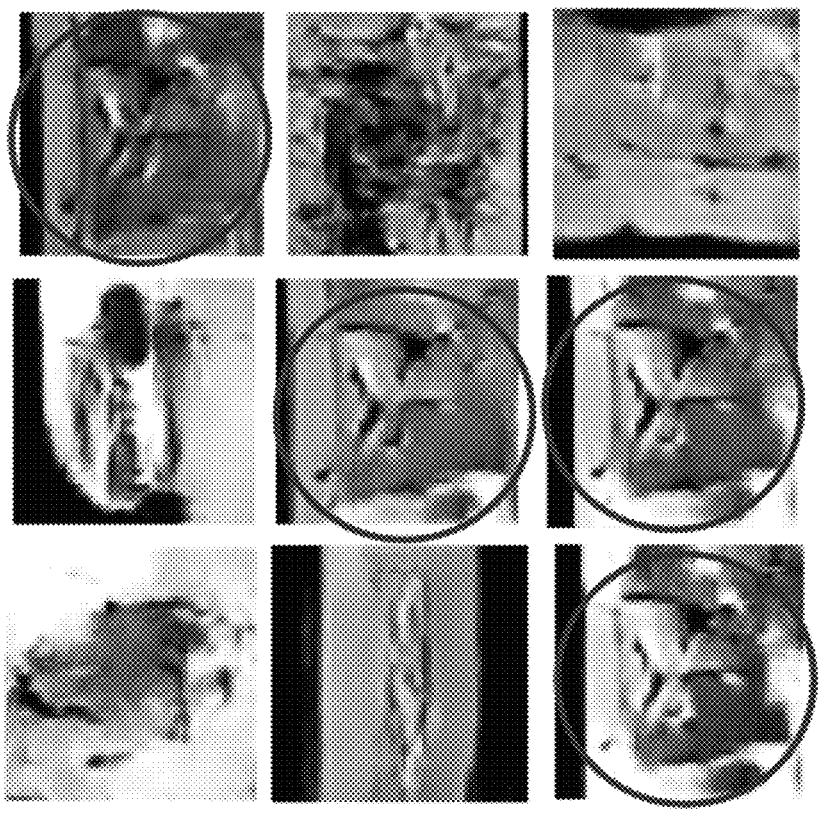
FIG. 12A shows exemplary generated representative images of several different NSCLC RNA samples. Specifically, some of the images, which are circled, include a common tripartite motif which represents a cluster.

FIG. 12A shows exemplary generated representative images of several different NSCLC RNA samples. Specifically, some of the images, which are circled, include a common tripartite motif which represents a cluster. FIG. 12B shows a two-dimensional t-SNE projection of a cohort of non-small-cell lung carcinoma (NSCLC) RNA samples encoded through a VAE. The samples with a tripartite motif are highlighted as squares (tripartite), while the samples with a high tumor purity are highlighted as triangles (high_close). It is noted that while the tripartite images typically cluster together, and mostly near the high tumor purity samples, there are noticeable outliers in both cases. These outliers indicate that the trained models described above (e.g., the trained model 508 in FIG. 5) can allow for the clustering of high-level features (such as the tripartite motif) that are not captured well through typical dimensionality reduction techniques (t-SNE).

RNA data is often subject to batch effects that complicate downstream analysis. For example, samples sequenced at two different labs may have subtle differences in a sequenced expression profile. Oftentimes, researchers will sequence a subset of samples in both labs and use a batch correction method to make one set of samples analytically more similar to that of the other lab. Exemplary batch correction methods include empirical Bayes methods, matching via mutual nearest neighbors, and scMerge.

Images generated using a trained generator can be used to inform which batch correction method is most suitable for a given problem. For example, a generator can be trained on expression profiles from Lab 1, and then used to create images for expression profiles from Lab 2, as well as the Lab 2 expression profiles transformed to resemble Lab 1 expression profiles using the batch correction methods. The batch correction method that produces expression profiles that result in the most similar images to those observed from Lab 1 can then be implemented to provide improved performance over other batch correction methods.

Figure 13A:
FIG. 13A is an exemplary representative image generated based on genetic data from a first sampling method of a tissue.
Figure 13B:
FIG. 13B is an example representative image generated based on genetic data from a second sampling method of the tissue.
Figure 13C:
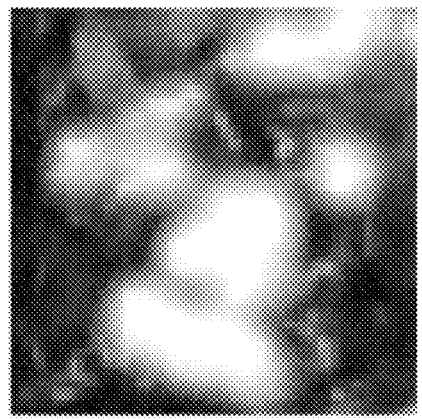
FIGS. 13C-E are exemplary images generated by various batch correction methods applied to RNA data.
Figure 13D:
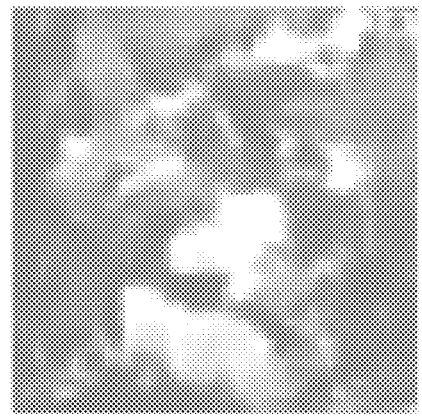
Figure 13E:
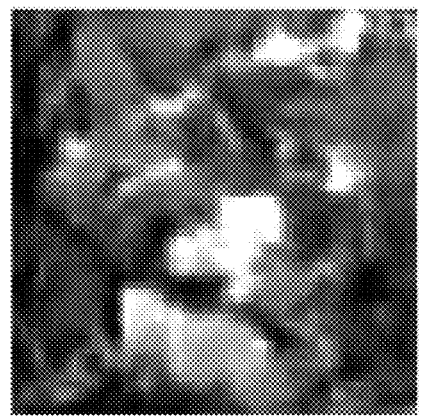

FIGS. 13A and 13B show images generated using a trained generator for an RNA sample sequenced in a first lab and a second lab, respectively. Several batch correction methods were trained on paired samples from the first lab and the second lab. Images generated based on corrected expression profiles (i.e., using different batch corrections methods) from the second lab are shown in FIGS. 13C-E. In this example, while the images in FIGS. 13C and 13D significantly distort or decolor the image, the image in FIG. 13E provides the most accurate recapitulation of both motifs present in the original images in FIGS. 13A and 13B without compromising the colors. Thus, the batch correction method used to generate the corrected expression profile associated with FIG. 13E may be the most effective batch correction method in this example.

Figures 14A, 14B:
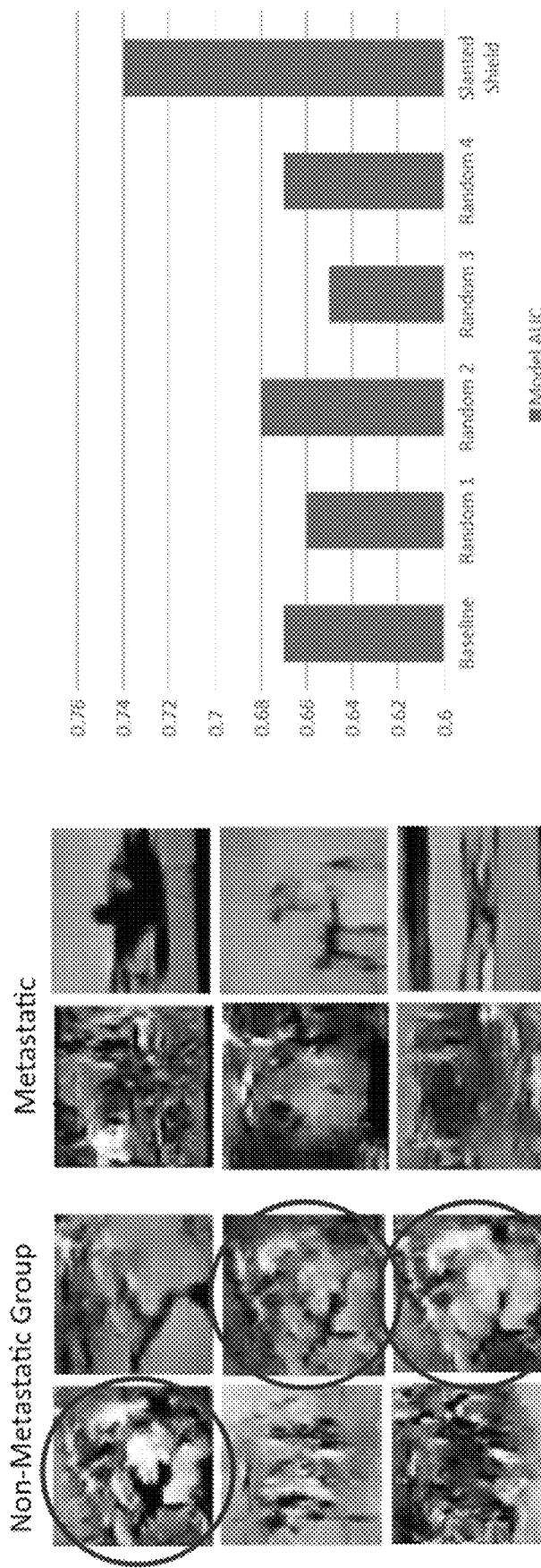
FIG. 14A shows two groups of representative images that have metastasized within 6 mo of sequencing and that did not.
FIG. 14B is a graph of associated area under the curve (AUC) for a baseline model.

FIG. 14A shows two groups of representative images, those that have metastasized within 6 months of sequencing and those that did not. Images exhibiting a 'slanted shield' motif that seems enriched in the non-metastatic group are circled. After labeling whether this motif is present across all samples, this feature can be used as part of model prediction, with the associated efficacy measured by a comparison to a random image motif selection.

The images in FIG. 14A are generated by a generator trained using a database of images unrelated to metastatic and non-metastatic patients and a database of patient information. The patient information can include latent space representations for a number of patients. In some embodiments, the latent space representations can include raw and/or reduced genetic data (e.g., RNA data) and/or other patient data as described above.

FIG. 14B shows a graph of associated area under the curve (AUC) for a baseline model, with labels from different random selections, and with the slanted shield motif. AUC measures overall model quality, with the slanted shield motif inclusion shows a significant increase in overall model predictiveness compared to baseline and other random selections.

Figure 15:
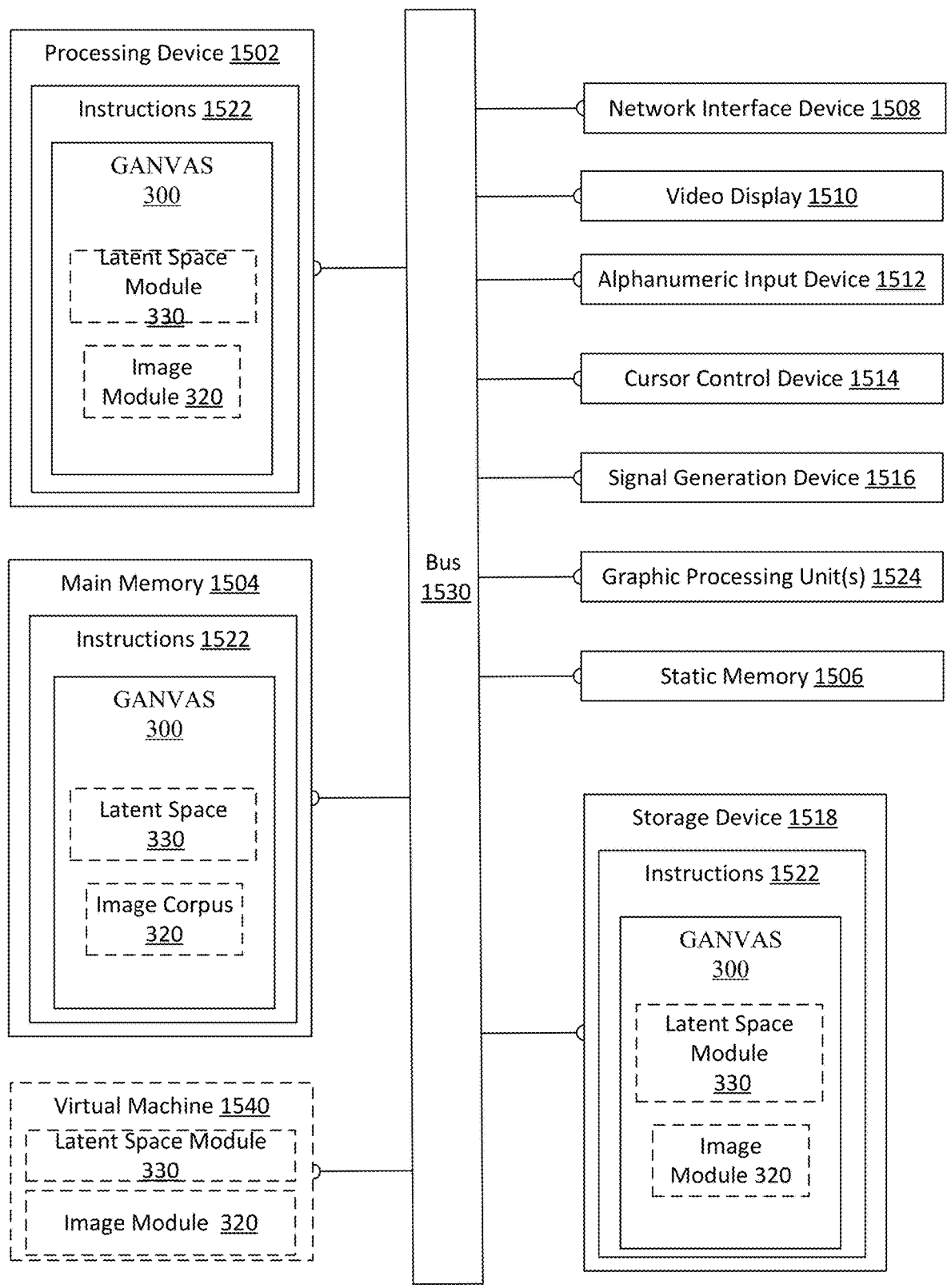
FIG. 15 is a block diagram of an implementation of a computer system in which some implementations of the disclosure may operate.

FIG. 15 shows a block diagram of an implementation of a computer system in which some implementations of the disclosure may operate. The example computer system 1500 includes a processing device 1502, a main memory 1504 (such as read-only memory (ROM), flash memory, dynamic random access memory (DRAM) such as synchronous DRAM (SDRAM) or DRAM, etc.), a static memory 1506 (such as flash memory, static random access memory (SRAM), etc.), and a data storage device 1518, which communicate with each other via a bus 1530.

Processing device 1502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1502 may also be one or more special-purpose processing devices such as an application specific integrated circuit (ASIC), a field programmable gate array (FPGA), a digital signal processor (DSP), network processor, or the like. The processing device 1502 is configured to execute instructions 1522 for performing the operations and steps discussed herein.

The computer system 1500 may further include a network interface device 1508 for connecting to the LAN, intranet, internet, and/or the extranet. The computer system 1500 also may include a video display unit 1510 (such as a liquid crystal display (LCD) or a cathode ray tube (CRT)), an alphanumeric input device 1512 (such as a keyboard), a cursor control device 1514 (such as a mouse), a signal generation device 1516 (such as a speaker), and a graphic processing unit 1524 (such as a graphics card).

The data storage device 1518 may be a machine-readable storage medium 1528 (also known as a computer-readable medium) on which is stored one or more sets of instructions or software 1522 embodying any one or more of the methodologies or functions described herein. The instructions 1522 may also reside, completely or at least partially, within the main memory 1504 and/or within the processing device 1502 during execution thereof by the computer system 1500, the main memory 1504 and the processing device 1502 also constituting machine-readable storage media.

In one implementation, the instructions 1522 include instructions for an image training set module (e.g., the image training set module 320 in FIG. 3) and/or a latent space extrapolation module (e.g., the latent space extrapolation module 330 in FIG. 3). The instructions 1522 can include a software library containing methods that function as an image training set module and/or a latent space extrapolation module.

While the machine-readable storage medium 1528 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine-readable storage medium as a transitory storage medium or transitory machine-readable storage medium.

In another implementation, a virtual machine 1540 may include a module for executing instructions for an image training set module and/or a latent space extrapolation module. In computing, a virtual machine (VM) is an emulation of a computer system. Virtual machines are based on computer architectures and provide functionality of a physical computer. Their implementations may involve specialized hardware, software, or a combination of hardware and software.

The systems and methods described herein can be used with other systems and methods for patient analysis. For example, groups and/or clusters generated as described above can be used as cohorts in order to produce the analytical user interfaces disclosed according to the system and method described in U.S. Patent Publication 2020/0211716, published Jul. 1, 2020, the contents of which are incorporated by reference herein in their entirety. In addition, the trained model 508 described above can be used with a device such as the devices disclosed in US Patent Publications 2020/0335102 and 2020/0335187, both published Oct. 21, 2020, the contents of which also are incorporated by reference herein in their entirety. Such a device may provide query support for related cohorts that are similar to the current subject based on groups and/or clusters generated as described above.

Moreover, image datasets such as training images and/or generated images can be stored in one or more data repositories, such as the lake database and/or the data vault database disclosed in U.S. Patent Publication 2021/0233664 ("the '664 publication"), which is a U.S. National Stage Entry of International Application PCT/US2019/056713, filed Oct. 17, 2019, the contents of both which are incorporated herein in their entirety. The resulting cohorts that are generated then may be stored in a data marts database, such as the data marts database disclosed in the '664 publication, and a metadata stream usable with the systems and methods of the '664 publication may include any of the features and/or outcomes (e.g., generated groups) as described above. Furthermore, the '664 publication discloses that its systems may include a plurality of different micro-services. Such micro-services may be employed to implement the training, calculating, subsequent analyzing, and the GUI presentation to a user disclosed herein. Other micro-services that may be employed to perform one or more of these activities further may be disclosed in U.S. Patent Publication 2020/0365232, published Nov. 18, 2020, and U.S. Patent Publication 2021/0090694 ("the '694 publication"), published Mar. 24, 2021, the contents of both which also are incorporated herein by reference in their entirety. Additionally, the systems and methods disclosed herein may employ the data or cohort normalization, bias correction, and batch correction methods disclosed in the '694 application, in combination with or instead of additional such methods as are known to those of ordinary skill in the relevant art. Furthermore, transformations including data normalization, bias correction, and batch correction methods are disclosed in U.S. Patent Publication 2020/0098448 ("the '448 publication"), published Mar. 26, 2020, the contents of which also are incorporated herein by reference in its entirety. Still further, transformations including spin adaptation are disclosed in U.S. Provisional Patent Application 63/067,748 ("the 748 application"), filed Aug. 19, 2020, the contents of which also are incorporated herein by reference in its entirety. The systems and methods disclosed herein may employ the transformations disclosed in the '448 publication and/or the 748 application, in combination with or instead of additional such methods as are known to those of ordinary skill in the relevant art.

The present disclosure has described one or more preferred embodiments, and it should be appreciated that many equivalents, alternatives, variations, and modifications, aside from those expressly stated, are possible and within the scope of the invention.

What is claimed is:

1. A method of analyzing a subject, the method comprising:
   receiving first genetic data comprising at least one of RNA data or DNA data associated with a subject;
   applying a machine learning model or a dimensionality reduction algorithm to the first genetic data to generate second genetic data having a lower dimensionality than the first genetic data;
   providing the second genetic data to a trained model;
   receiving a subject image generated by the trained model using the second genetic data;
   identifying a pattern in the subject image that is present in at least one other image in a set of images generated by the trained model;
   providing the subject image to an analysis engine;
   receiving subject information from the analysis engine; and
   causing the subject information to be output to at least one of a medical practitioner or a memory.

2. The method of claim 1, wherein the first genetic data comprises at least one thousand RNA expression levels, and wherein the second genetic data comprises no more than one hundred dimensions of values.

3. The method of claim 1, wherein applying a machine learning model or a dimensionality reduction algorithm to the first genetic data to generate second genetic data comprises:
   providing the first genetic data to a trained autoencoder; and
   receiving the second genetic data from the trained autoencoder.

4. The method of claim 1, wherein the trained model comprises a neural network.

5. The method of claim 4, wherein the neural network is a U-Net.

6. The method of claim 1, wherein the trained model comprises a generator comprising a neural network, the generator being previously trained by training a training model comprising the generator and a discriminator based on a set of latent space representations and a set of images.

7. The method of claim 1, wherein applying a machine learning model or a dimensionality reduction algorithm to the first genetic data to generate second genetic data comprises: applying one or more of principal component analysis (PCA) or t-distributed stochastic neighbor embedding to the first genetic data.

8. The method of claim 6, wherein each latent space representation included in the set of latent space representations is generated by a trained autoencoder, and wherein the second genetic data comprises a latent space representation generated by the trained autoencoder.

9. The method of claim 6, wherein the training the training model comprises:
providing a latent space representation included in the set of latent space representations to the generator;
receiving a generated image from the generator;
providing the generated image and an image included in the set of images to the discriminator; and
updating weights included in the generator and the discriminator based on the generated image and the image included in the set of images to the discriminator.

10. The method of claim 9, wherein the set of images comprises object images.

11. The method of claim 10, wherein the set of images comprises object images comprises images of at least one of an airplane, a bird, a car, a cat, a deer, a dog, a horse, a monkey, a ship, or a truck.

12. The method of claim 6, wherein the set of images comprises cell images.

13. The method of claim 12, wherein the cell images comprise slide images.

14. The method of claim 1, wherein the subject information comprises information from a cohort of patients subjects.

15. The method of claim 1, wherein the subject information comprises at least one potential treatment for the subject.

16. The method of claim 1, wherein the identifying the pattern in the subject image comprises clustering the subject image with a subset of the set of images generated by the trained model.

17. The method of claim 16, wherein the analysis engine is configured to identify at least one diagnostic metric between the subject image and a group of patients subjects associated with the subset of the set of images.

18. The method of claim 17, wherein the at least one diagnostic metric comprises at least one of a gene variant present in the subject and at least a portion of the group of patients subjects, a disease present in the subject and at least a portion of the group of patients subjects, a preexisting condition present in the subject and at least a portion of the group of patients subjects, a treatment provided to at least a portion of the group of patients subjects, or a trial participated in by at least a portion of the group of patients subjects.

19. A system for analyzing a subject, the system comprising:
at least one memory; and
at least one processor coupled to the at least one memory, the system configured to cause the at least one processor to execute instructions stored in the at least one memory to:
receive first genetic data comprising at least one of RNA data or DNA data associated with a subject;
generate apply a machine learning model or a dimensionality reduction algorithm to the first genetic data to generate second genetic data having a lower dimensionality than the first genetic data;
provide the second genetic data to a trained model;
receive a subject image generated by the trained model using the second genetic data;
identify a pattern in the subject image that is present in at least one other image in a set of images generated by the trained model;
provide the subject image to an analysis engine;
receive subject information from the analysis engine; and
cause the subject information to be output to at least one of a medical practitioner or a memory.

20. A computer program product for analyzing a subject, the computer program product comprising instructions stored on a non-transitory computer readable medium to cause at least one processor to:
receive first genetic data comprising at least one of RNA data or DNA data associated with a subject;
apply a machine learning model or a dimensionality reduction algorithm to the first genetic data to generate second genetic data having a lower dimensionality than the first genetic data;
provide the second genetic data to a trained model;
receive a subject image generated by the trained model using the second genetic data;
identify a pattern in the subject image that is present in at least one other image in a set of images generated by the trained model;
provide the subject image to an analysis engine;
receive subject information from the analysis engine; and
cause the subject information to be output to at least one of a medical practitioner or a memory.

* * * * *